United States Patent [19]

Tajima et al.

[11] Patent Number: 5,506,205
[45] Date of Patent: Apr. 9, 1996

[54] POLYPEPTIDE OF PROTEIN P140 AND DNAS ENCODING IT

[75] Inventors: Hisao Tajima; Koichiro Kitagawa; Hiroyuki Ohno, all of Osaka, Japan

[73] Assignee: Ono Pharmaceutical Co., Ltd., Osaka, Japan

[21] Appl. No.: 348,143

[22] Filed: Nov. 23, 1994

[30] Foreign Application Priority Data

Nov. 24, 1993 [JP] Japan .................................. 5-315806

[51] Int. Cl.$^6$ ...................... A61K 38/00; C07K 14/435; C12N 9/12
[52] U.S. Cl. .............................. 514/12; 530/350; 435/194
[58] Field of Search ................................ 514/12; 530/350

[56] References Cited

U.S. PATENT DOCUMENTS 5,260,200  11/1993  Kahn et al. .............................. 435/68.1

*Primary Examiner*—Robert A. Wax
*Assistant Examiner*—Kawai Lau
*Attorney, Agent, or Firm*—Sughrue, Mion, Zinn, Macpeak & Seas

[57] ABSTRACT

The present invention is related to a novel protein p140 polypeptide which is a key protein involved in the signal transmission system of insulin; method for preparation of it; DNA encoding the said polypeptide; vector comprising the DNA; host cells transformed with the vector; antibody against the polypeptide; pharmaceutical compositions containing the peptide or antibody; method for the prevention and/or treatment of diabetes, which is characterized by tyrosine phosphorylation of the said protein p140; agent for the prevention and/or treatment of diabetes, which is characterized by containing a compound which can tyrosine phosphorylate protein p140, as active ingredient and screening methods for the prevention and/or treatment agent.

Tyrosine phosphorylation of protein p140 is an essential step in the induction of hypoglycemia by glucose uptake. Method and agent of prevention and/or treatment based on tyrosine phosphorylation of protein p140 in the present invention is not only to improves the diabetes-derived hyperglycemic conditions but are also useful for the treatment and/or prevention of diabetes, especially non-insulin dependent diabetes mellitus (NIDDM).

2 Claims, 3 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 993 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: rat
        ( F ) TISSUE TYPE: skeletal muscle myoblast
        ( H ) CELL LINE: L6

( x i ) SEQUENCE DESCRIPTION: SEQ ID NO:1:

| Met | Glu | Asn | Pro | Tyr | Val | Gly | Arg | Ala | Arg | Ala | Ala | Ala | Glu | Arg | Ala |
|---|---|---|---|---|---|---|---|---|---|---|---|---|---|---|---|
| 1 | | | | 5 | | | | | 10 | | | | | 15 | |

| Ala | Ala | Glu | Ala | Thr | Asn | Ser | Leu | Ser | Ile | Leu | Val | Arg | Pro | Thr | Ser |
|---|---|---|---|---|---|---|---|---|---|---|---|---|---|---|---|
| | | | 20 | | | | | 25 | | | | | 30 | | |

| Glu | Gly | Ser | Arg | Ile | Asp | Ser | Glu | Phe | Val | Glu | Leu | Ala | Trp | Thr | Ser |
|---|---|---|---|---|---|---|---|---|---|---|---|---|---|---|---|
| | | 35 | | | | | 40 | | | | | 45 | | | |

| His | Pro | Glu | Ser | Gly | Trp | Glu | Glu | Val | Ser | Ala | Tyr | Asp | Glu | Ala | Met |
|---|---|---|---|---|---|---|---|---|---|---|---|---|---|---|---|
| | 50 | | | | | | 55 | | | | | 60 | | | |

| Asn | Pro | Ile | Arg | Thr | Tyr | Gln | Val | Cys | Asn | Val | Arg | Glu | Ser | Ser | Gln |
|---|---|---|---|---|---|---|---|---|---|---|---|---|---|---|---|
| 65 | | | | | 70 | | | | | 75 | | | | | 80 |

| Asn | Asn | Trp | Leu | Arg | Thr | Gly | Phe | Ile | Trp | Arg | Arg | Glu | Val | Gln | Arg |
|---|---|---|---|---|---|---|---|---|---|---|---|---|---|---|---|
| | | | | 85 | | | | | 90 | | | | | 95 | |

| Val | Tyr | Val | Glu | Leu | Lys | Phe | Thr | Val | Arg | Asp | Cys | Asn | Ser | Ile | Pro |
|---|---|---|---|---|---|---|---|---|---|---|---|---|---|---|---|
| | | | 100 | | | | | 105 | | | | | 110 | | |

| Asn | Ile | Pro | Gly | Ser | Cys | Lys | Glu | Thr | Phe | Asn | Leu | Phe | Tyr | Tyr | Glu |
|---|---|---|---|---|---|---|---|---|---|---|---|---|---|---|---|
| | | 115 | | | | | 120 | | | | | 125 | | | |

| Ala | Asp | Ser | Asp | Val | Ala | Ser | Ala | Ser | Ser | Pro | Phe | Trp | Met | Glu | Asn |
|---|---|---|---|---|---|---|---|---|---|---|---|---|---|---|---|
| | 130 | | | | | 135 | | | | | 140 | | | | |

| Pro | Tyr | Val | Lys | Val | Asp | Thr | Ile | Ala | Pro | Asp | Glu | Ser | Phe | Ser | Arg |
|---|---|---|---|---|---|---|---|---|---|---|---|---|---|---|---|
| 145 | | | | | 150 | | | | | 155 | | | | | 160 |

| Leu | Asp | Ala | Gly | Arg | Val | Asn | Thr | Lys | Val | Arg | Ser | Phe | Gly | Pro | Leu |
|---|---|---|---|---|---|---|---|---|---|---|---|---|---|---|---|
| | | | | 165 | | | | | 170 | | | | | 175 | |

| Ser | Lys | Ala | Gly | Phe | Tyr | Leu | Ala | Phe | Gln | Asp | Gln | Gly | Ala | Cys | Met |
|---|---|---|---|---|---|---|---|---|---|---|---|---|---|---|---|
| | | | 180 | | | | | 185 | | | | | 190 | | |

| Ser | Leu | Ile | Ser | Val | Arg | Ala | Phe | Tyr | Lys | Lys | Cys | Ala | Ser | Thr | Thr |
|---|---|---|---|---|---|---|---|---|---|---|---|---|---|---|---|
| | | 195 | | | | | 200 | | | | | 205 | | | |

| Ala | Gly | Phe | Ala | Leu | Phe | Pro | Glu | Thr | Leu | Thr | Gly | Ala | Glu | Pro | Thr |
|---|---|---|---|---|---|---|---|---|---|---|---|---|---|---|---|
| | 210 | | | | | 215 | | | | | 220 | | | | |

| Ser | Leu | Val | Ile | Ala | Pro | Gly | Thr | Cys | Ile | Ala | Asn | Ala | Val | Glu | Val |
|---|---|---|---|---|---|---|---|---|---|---|---|---|---|---|---|
| 225 | | | | | 230 | | | | | 235 | | | | | 240 |

| Ser | Val | Pro | Leu | Lys | Leu | Tyr | Cys | Asn | Gly | Asp | Gly | Glu | Trp | Met | Val |
|---|---|---|---|---|---|---|---|---|---|---|---|---|---|---|---|
| | | | | 245 | | | | | 250 | | | | | 255 | |

| Pro | Val | Gly | Ala | Cys | Thr | Cys | Ala | Thr | Gly | His | Glu | Pro | Ala | Ala | Lys |
|---|---|---|---|---|---|---|---|---|---|---|---|---|---|---|---|
| | | | 260 | | | | | 265 | | | | | 270 | | |

| Glu | Thr | Gln | Cys | Arg | Ala | Cys | Pro | Pro | Gly | Ser | Tyr | Lys | Ala | Lys | Gln |
|---|---|---|---|---|---|---|---|---|---|---|---|---|---|---|---|
| | | 275 | | | | | 280 | | | | | 285 | | | |

| Gly | Glu | Gly | Pro | Cys | Leu | Pro | Cys | Pro | Pro | Asn | Ser | Arg | Thr | Thr | Ser |
|---|---|---|---|---|---|---|---|---|---|---|---|---|---|---|---|
| | 290 | | | | | 295 | | | | | 300 | | | | |

| Pro | Ala | Ala | Ser | Ile | Cys | Thr | Cys | His | Asn | Asn | Phe | Tyr | Arg | Ala | Asp |
|---|---|---|---|---|---|---|---|---|---|---|---|---|---|---|---|
| 305 | | | | | 310 | | | | | 315 | | | | | 320 |

| Ser | Asp | Thr | Ala | Asp | Ser | Ala | Cys | Thr | Thr | Val | Pro | Ser | Pro | Pro | Arg |
|---|---|---|---|---|---|---|---|---|---|---|---|---|---|---|---|
| | | | | 325 | | | | | 330 | | | | | 335 | |

| Gly | Val | Ile | Ser | Asn | Val | Asn | Glu | Thr | Ser | Leu | Ile | Leu | Glu | Trp | Ser |
|---|---|---|---|---|---|---|---|---|---|---|---|---|---|---|---|
| | | | 340 | | | | | 345 | | | | | 350 | | |

| Glu | Pro | Arg | Asp | Leu | Gly | Gly | Arg | Asp | Asp | Leu | Leu | Tyr | Asn | Val | Ile |
|---|---|---|---|---|---|---|---|---|---|---|---|---|---|---|---|
| | | 355 | | | | | 360 | | | | | 365 | | | |

| Cys | Lys | Lys | Cys | Arg | Gly | Ser | Ser | Gly | Ala | Gly | Pro | Ala | Thr | Cys |
|---|---|---|---|---|---|---|---|---|---|---|---|---|---|---|
| 370 | | | | | 375 | | | | | 380 | | | | |

| Ser | Arg | Cys | Asp | Asp | Asn | Val | Glu | Phe | Glu | Pro | Arg | Gln | Leu | Gly | Leu |
|---|---|---|---|---|---|---|---|---|---|---|---|---|---|---|---|
| 385 | | | | | 390 | | | | | 395 | | | | | 400 |

| Thr | Glu | Arg | Arg | Val | His | Ile | Ser | His | Leu | Leu | Ala | His | Thr | Arg | Tyr |
|---|---|---|---|---|---|---|---|---|---|---|---|---|---|---|---|
| | | | | 405 | | | | | 410 | | | | | 415 | |

| Thr | Phe | Glu | Val | Gln | Ala | Val | Asn | Gly | Val | Ser | Gly | Lys | Ser | Pro | Leu |
|---|---|---|---|---|---|---|---|---|---|---|---|---|---|---|---|
| | | | 420 | | | | | 425 | | | | | 430 | | |

```
Pro  Pro  Arg  Tyr  Ala  Ala  Val  Asn  Ile  Thr  Thr  Asn  Gln  Ala  Ala  Pro
          435                 440                      445

Ser  Glu  Val  Pro  Thr  Leu  His  Leu  His  Ser  Ser  Ser  Gly  Ser  Ser  Leu
          450                 455                      460

Thr  Leu  Ser  Trp  Ala  Pro  Pro  Glu  Arg  Pro  Asn  Gly  Val  Ile  Leu  Asp
465                      470                 475                           480

Tyr  Glu  Met  Lys  Tyr  Phe  Glu  Lys  Ser  Lys  Gly  Ile  Ala  Ser  Thr  Val
                    485                      490                      495

Thr  Ser  Gln  Lys  Asn  Ser  Val  Gln  Leu  Asp  Gly  Leu  Gln  Pro  Asp  Ala
                    500                 505                      510

Arg  Tyr  Val  Val  Gln  Val  Arg  Ala  Arg  Thr  Val  Ala  Gly  Tyr  Gly  Gln
               515                 520                      525

Tyr  Ser  Arg  Pro  Ala  Glu  Phe  Glu  Thr  Thr  Ser  Glu  Arg  Gly  Ser  Gly
          530                 535                      540

Ala  Gln  Gln  Leu  Gln  Glu  Gln  Leu  Pro  Leu  Ile  Val  Gly  Ser  Thr  Val
545                      550                 555                           560

Ala  Gly  Phe  Val  Phe  Met  Val  Val  Val  Val  Val  Ile  Ala  Leu  Val  Cys
                         565                 570                      575

Leu  Arg  Lys  Gln  Arg  Gln  Gly  Pro  Asp  Ala  Glu  Tyr  Thr  Glu  Lys  Leu
               580                 585                      590

Gln  Gln  Tyr  Val  Ala  Pro  Arg  Met  Lys  Val  Tyr  Ile  Asp  Pro  Phe  Thr
          595                 600                      605

Tyr  Glu  Asp  Pro  Asn  Glu  Ala  Val  Arg  Glu  Phe  Ala  Lys  Glu  Ile  Asp
          610                 615                      620

Val  Ser  Cys  Val  Lys  Ile  Glu  Glu  Val  Ile  Gly  Ala  Gly  Glu  Phe  Gly
625                      630                 635                           640

Glu  Val  Cys  Arg  Gly  Arg  Leu  Lys  Leu  Pro  Gly  Arg  Arg  Glu  Val  Phe
                    645                 650                      655

Val  Ala  Ile  Lys  Thr  Leu  Lys  Val  Gly  Tyr  Thr  Glu  Arg  Gln  Arg  Arg
                    660                 665                      670

Asp  Phe  Leu  Ser  Glu  Ala  Ser  Ile  Met  Gly  Gln  Phe  Asp  His  Pro  Asn
          675                 680                      685

Ile  Ile  Arg  Leu  Glu  Gly  Val  Thr  Lys  Ser  Arg  Pro  Val  Met  Ile
690                      695                 700

Leu  Thr  Glu  Phe  Met  Glu  Asn  Cys  Ala  Leu  Asp  Ser  Phe  Leu  Arg  Leu
705                      710                 715                           720

Asn  Asp  Gly  Gln  Phe  Thr  Val  Ile  Gln  Leu  Val  Gly  Met  Leu  Arg  Gly
                    725                 730                      735

Ile  Ala  Ala  Gly  Met  Lys  Tyr  Leu  Ser  Glu  Met  Asn  Tyr  Val  His  Arg
               740                 745                      750

Asp  Leu  Ala  Ala  Arg  Asn  Ile  Leu  Val  Asn  Ser  Asn  Leu  Val  Cys  Lys
          755                 760                      765

Val  Ser  Asp  Phe  Gly  Leu  Ser  Arg  Phe  Leu  Glu  Asp  Asp  Pro  Ser  Asp
     770                 775                      780

Pro  Thr  Tyr  Thr  Ser  Ser  Leu  Gly  Gly  Lys  Ile  Pro  Ile  Arg  Trp  Thr
785                      790                 795                           800

Ala  Pro  Glu  Ala  Ile  Asp  Tyr  Arg  Lys  Phe  Thr  Ser  Ala  Ser  Asp  Val
                    805                 810                      815

Trp  Ser  Tyr  Gly  Ile  Val  Met  Trp  Glu  Val  Met  Ser  Tyr  Gly  Glu  Arg
               820                 825                      830

Pro  Tyr  Trp  Asp  Met  Ser  Asn  Gln  Asp  Val  Ile  Asn  Ala  Val  Glu  Gln
          835                 840                      845

Asp  Tyr  Arg  Leu  Pro  Pro  Pro  Met  Asp  Cys  Pro  Ala  Ala  Leu  His  Gln
```

|     |     |     |     | 850 |     |     |     |     | 855 |     |     |     |     | 860 |     |
| --- | --- | --- | --- | --- | --- | --- | --- | --- | --- | --- | --- | --- | --- | --- | --- |

Leu Met Leu Asp Cys Trp Val Arg Asp Arg Asn Leu Arg Pro Lys Phe
865                     870             875                 880

Ser Gln Ile Val Asn Thr Leu Asp Lys Leu Ile Arg Asn Ala Ala Ser
                885             890                     895

Leu Lys Val Ile Ala Ser Ala Pro Ser Gly Met Ser Gln Pro Leu Leu
            900             905                 910

Asp Arg Thr Val Pro Asp Tyr Thr Thr Phe Thr Thr Val Gly Asp Trp
        915             920             925

Leu Asp Ala Ile Lys Met Gly Arg Tyr Lys Glu Ser Phe Val Gly Ala
    930             935             940

Gly Phe Ala Ser Phe Asp Leu Val Ala Gln Met Thr Ala Glu Asp Leu
945             950             955                         960

Leu Arg Ile Gly Val Thr Leu Ala Gly His Gln Lys Lys Ile Leu Ser
                965             970                     975

Ser Ile Gln Asp Met Arg Leu Gln Met Asn Gln Thr Leu Pro Val Gln
            980             985                 990

Val ( 2 ) INFORMATION FOR SEQ ID NO:2:

( i ) SEQUENCE CHARACTERISTICS:
        ( A ) LENGTH: 2982 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: rat
        ( F ) TISSUE TYPE: skeletal muscle myoblast
        ( H ) CELL LINE: L6

( x i ) SEQUENCE DESCRIPTION: SEQ ID NO:2:

```
ATGGAGAACC CTACGTTGG  GCGAGCGAGA GCAGCAGCGG AGCGAGCAGC GGCAGAAGCC      60
ACGAATTCAC TATCGATCCT GGTTCGGCCC ACCTCTGAAG GTTCCAGAAT CGATAGTGAA     120
TTCGTGGAGC TGGCATGGAC ATCTCATCCA GAGAGTGGGT GGGAAGAAGT GAGCGCCTAC     180
GATGAAGCCA TGAATCCTAT CCGCACGTAT CAGGTGTGTA ACGTGCGCGA GTCCAGCCAG     240
AACAACTGGC TGCGGACCGG TTTCATCTGG CGGCGGGAAG TCCAGCGCGT CTACGTGGAG     300
CTGAAGTTTA CCGTGAGAGA TTGCAACAGC ATCCCCAACA TCCCTGGCTC CTGCAAGGAA     360
ACCTTCAACC TTTTTTACTA CGAGGCTGAT AGCGATGTGG CGTCAGCCTC CTCTCCCTTC     420
TGGATGGAGA ACCCCTACGT GAAAGTGGAC ACCATTGCGC AGATGAGAG  CTTCTCGCGG     480
CTAGACGCTG GGCGCGTTAA CACCAAAGTG CGCAGCTTCG GCCGCTTTC  CAAAGCCGGC     540
TTCTACTTGG CCTTCCAGGA CCAGGGTGCC TGCATGTCAC TCATCTCTGT GCGCGCCTTC     600
TACAAGAAGT GTGCATCCAC CACTGCAGGC TTCGCACTCT CCCCGAGAC  CCTCACGGGG     660
GCTGAGCCCA CTTCGCTGGT CATTGCCCCT GGCACCTGCA TCGCTAACGC TGTGGAGGTG     720
TCTGTACCGC TCAAGCTCTA CTGCAATGGC GACGGGGAGT GGATGGTGCC CGTTGGTGCC     780
TGCACCTGCG CTACTGGCCA TGAGCCAGCC GCCAAGGAGA CCCAGTGCCG CGCCTGTCCC     840
CCTGGGAGCT ACAAGGCAAA GCAAGGAGAG GGGCCCTGCC TCCCCTGTCC CCCCAATAGC     900
CGCACCACCT CGCCGGCTGC CAGCATCTGC ACCTGTCACA ATAATTTCTA CCGCGCAGAC     960
TCAGACACAG CGGACAGCGC CTGCACCACG GTGCCGTCTC CCCCCCGGGG TGTGATCTCC    1020
```

| | | | | | | |
|---|---|---|---|---|---|---|
| AATGTGAATG | AGACCTCGCT | GATCCTCGAG | TGGAGTGAGC | CCCGGGACCT | TGGCGGACGA | 1080 |
| GATGACCTCC | TTTATAATGT | TATCTGTAAG | AAGTGCCGTG | GCAGCTCTGG | GGCTGGAGGT | 1140 |
| CCGGCGACCT | GTTCACGCTG | TGATGACAAC | GTGGAGTTCG | AGCCCCGACA | GCTGGGCCTG | 1200 |
| ACCGAGCGCC | GGGTCCACAT | CAGCCACCTG | TTGGCCCACA | CCCGCTACAC | CTTTGAGGTG | 1260 |
| CAGGCTGTCA | ACGGCGTCTC | TGGCAAAAGC | CCTTTGCCGC | CCCGCTATGC | AGCTGTGAAT | 1320 |
| ATCACCACCA | ACCAGGCCGC | CCCATCAGAA | GTGCCTACGC | TCCACTTGCA | CAGCAGTTCA | 1380 |
| GGGAGCAGCC | TGACCCTGTC | CTGGGCACCC | CCGGAGCGGC | CTAACGGAGT | CATCTTGGAC | 1440 |
| TATGAGATGA | AGTACTTTGA | GAAGAGTAAA | GGCATCGCCT | CCACTGTCAC | CAGCCAGAAG | 1500 |
| AACTCTGTAC | AACTGGACGG | ACTGCAGCCC | GACGCCGCT | ATGTAGTTCA | GGTCCGGGCT | 1560 |
| CGCACAGTAG | CAGGTTACGG | ACAGTATAGC | CGCCCAGCTG | AGTTTGAGAC | CACGAGTGAA | 1620 |
| AGAGGCTCAG | GGGCCCAGCA | GCTTCAAGAG | CAGCTTCCCC | TAATTGTGGG | ATCCACCGTA | 1680 |
| GCTGGCTTTG | TCTTCATGGT | GGTCGTCGTG | GTCATTGCTC | TTGTCTGCCT | CAGGAAGCAG | 1740 |
| CGCCAGGGCC | CTGATGCAGA | ATACACGGAG | AAGTTGCAGC | AATACGTTGC | CCCCAGGATG | 1800 |
| AAAGTTTACA | TTGACCCCTT | TACCTACGAG | GATCCCAATG | AGGCCGTCCG | AGAGTTCGCC | 1860 |
| AAGGAGATCG | ATGTGTCCTG | CGTCAAGATC | GAGGAGGTGA | TTGGAGCTGG | GGAGTTTGGG | 1920 |
| GAAGTGTGCC | GGGGTCGGCT | GAAACTGCCC | GGCCGCCGGG | AGGTGTTCGT | GGCCATCAAG | 1980 |
| ACACTGAAGG | TGGGATACAC | GGAGAGGCAG | CGGCGGGACT | TCCTGAGTGA | GGCTTCCATC | 2040 |
| ATGGGTCAAT | TTGACCATCC | AAATATAATC | CGTCTAGAGG | GCGTGGTCAC | CAAAAGTCGT | 2100 |
| CCAGTCATGA | TCCTCACTGA | GTTCATGGAG | AACTGTGCCC | TGGACTCCTT | CCTACGGCTC | 2160 |
| AATGACGGGC | AGTTCACAGT | CATCCAGCTT | GTGGGCATGT | TGCGTGGCAT | TGCTGCCGGC | 2220 |
| ATGAAGTACT | TGTCTGAGAT | GAACTACGTG | CACCGTGACC | TCGCTGCCCG | CAACATCCTT | 2280 |
| GTCAACAGTA | ACTTGGTCTG | CAAAGTATCT | GACTTTGGGC | TCTCCCGCTT | CCTGGAGGAC | 2340 |
| GACCCCTCAG | ACCCCACCTA | CACCAGCTCC | CTGGGTGGGA | AGATCCCTAT | CCGTTGGACC | 2400 |
| GCCCCAGAGG | CCATAGACTA | TCGGAAGTTC | ACGTCTGCCA | GCGATGTCTG | GAGCTACGGG | 2460 |
| ATCGTCATGT | GGGAGGTCAT | GAGCTACGGA | GAGCGACCAT | ACTGGGACAT | GAGCAACCAG | 2520 |
| GATGTCATCA | ATGCCGTAGA | GCAAGACTAT | CGGTTACCAC | CCCCCATGGA | CTGCCCAGCG | 2580 |
| GCGCTGCACC | AGCTCATGCT | GGACTGTTGG | GTGCGGGACC | GGAACCTCAG | GCCCAAGTTC | 2640 |
| TCCCAAATCG | TCAACACGCT | AGACAAGCTT | ATCCGCAATG | CTGCCAGCCT | CAAGGTCATC | 2700 |
| GCCAGTGCCC | CATCTGGCAT | GTCCCAGCCC | CTCCTAGACC | GCACGGTCCC | AGATTATACG | 2760 |
| ACCTTCACGA | CGGTGGGCGA | CTGGCTAGAT | GCCATCAAGA | TGGGGAGGTA | TAAAGAGAGC | 2820 |
| TTCGTCGGTG | CGGGTTTTGC | CTCCTTTGAC | CTGGTGGCCC | AGATGACTGC | AGAAGATCTG | 2880 |
| CTAAGGATCG | GGGTCACTTT | GGCCGGCCAC | CAGAAGAAGA | TCCTCAGCAG | TATCCAGGAC | 2940 |
| ATGCGGCTGC | AGATGAACCA | GACACTGCCC | GTGCAGGTCT | GA | | 2982 |

( 2 ) INFORMATION FOR SEQ ID NO:3:

( i ) SEQUENCE CHARACTERISTICS:
        ( A ) LENGTH: 4027 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: rat
        ( F ) TISSUE TYPE: skeletal muscle myoblast ( H ) CELL LINE: L6

( x i ) SEQUENCE DESCRIPTION: SEQ ID NO:3:

| | | | | | | |
|---|---|---|---|---|---|---|
| GAAAAATGAA | GATCTATACC | GACAGCAGAT | CAGTGGCTGC | CTGGGGCAAA | GTTGGAGGGA | 60 |
| CATGTTATTT | TGATTGTGAT | GACATAATAC | ATGCAAACAC | GGCTAATCCT | CTCAAAGCAT | 120 |
| ACACTTATAC | ATGTGCAGCT | TGGTATACAT | AAATTATCCA | TTACAAAACT | ATGAGAAAGC | 180 |
| TATCACCACT | ATGAAGCACC | ACTCACAGTA | TGTGAATCTC | CACCCCCTT | CCACTGCTGA | 240 |
| GACACAGAAA | TCCTAGACTG | GATGGAGAAC | CCCTACGTTG | GGCGAGCGAG | AGCAGCAGCG | 300 |
| GAGCGAGCAG | CGGCAGAAGC | CACGAATTCA | CTATCGATCC | TGGTTCGGCC | CACCTCTGAA | 360 |
| GGTTCCAGAA | TCGATAGTGA | ATTCGTGGAG | CTGGCATGGA | CATCTCATCC | AGAGAGTGGG | 420 |
| TGGGAAGAAG | TGAGCGCCTA | CGATGAAGCC | ATGAATCCTA | TCCGCACGTA | TCAGGTGTGT | 480 |
| AACGTGCGCG | AGTCCAGCCA | GAACAACTGG | CTGCGGACCG | GTTTCATCTG | GCGGCGGGAA | 540 |
| GTCCAGCGCG | TCTACGTGGA | GCTGAAGTTT | ACCGTGAGAG | ATTGCAACAG | CATCCCCAAC | 600 |
| ATCCCTGGCT | CCTGCAAGGA | AACCTTCAAC | CTTTTTTACT | ACGAGGCTGA | TAGCGATGTG | 660 |
| GCGTCAGCCT | CCTCTCCCTT | CTGGATGGAG | AACCCCTACG | TGAAAGTGGA | CACCATTGCG | 720 |
| CCAGATGAGA | GCTTCTCGCG | GCTAGACGCT | GGGCGCGTTA | ACACCAAAGT | GCGCAGCTTC | 780 |
| GGGCCGCTTT | CCAAAGCCGG | CTTCTACTTG | GCCTTCCAGG | ACCAGGGTGC | CTGCATGTCA | 840 |
| CTCATCTCTG | TGCGCGCCTT | CTACAAGAAG | TGTGCATCCA | CCACTGCAGG | CTTCGCACTC | 900 |
| TTCCCCGAGA | CCCTCACGGG | GGCTGAGCCC | ACTTCGCTGG | TCATTGCCCC | TGGCACCTGC | 960 |
| ATCGCTAACG | CTGTGGAGGT | GTCTGTACCG | CTCAAGCTCT | ACTGCAATGG | CGACGGGGAG | 1020 |
| TGGATGGTGC | CCGTTGGTGC | CTGCACCTGC | GCTACTGGCC | ATGAGCCAGC | CGCCAAGGAG | 1080 |
| ACCCAGTGCC | GCGCCTGTCC | CCCTGGGAGC | TACAAGGCAA | AGCAAGGAGA | GGGGCCCTGC | 1140 |
| CTCCCCTGTC | CCCCCAATAG | CCGCACCACC | TCGCCGGCTG | CCAGCATCTG | CACCTGTCAC | 1200 |
| AATAATTTCT | ACCGCGCAGA | CTCAGACACA | GCGGACAGCG | CCTGCACCAC | GGTGCCGTCT | 1260 |
| CCCCCCCGGG | GTGTGATCTC | CAATGTGAAT | GAGACCTCGC | TGATCCTCGA | GTGGAGTGAG | 1320 |
| CCCCGGGACC | TTGGCGGACG | AGATGACCTC | CTTTATAATG | TTATCTGTAA | GAAGTGCCGT | 1380 |
| GGCAGCTCTG | GGGCTGGAGG | TCCGGCGACC | TGTTCACGCT | GTGATGACAA | CGTGGAGTTC | 1440 |
| GAGCCCCGAC | AGCTGGGCCT | GACCGAGCGC | CGGGTCCACA | TCAGCCACCT | GTTGGCCCAC | 1500 |
| ACCCGCTACA | CCTTTGAGGT | GCAGGCTGTC | AACGGCGTCT | CTGGCAAAAG | CCCTTTGCCG | 1560 |
| CCCCGCTATG | CAGCTGTGAA | TATCACCACC | AACCAGGCCG | CCCCATCAGA | AGTGCCTACG | 1620 |
| CTCCACTTGC | ACAGCAGTTC | AGGGAGCAGC | CTGACCCTGT | CCTGGGCACC | CCCGGAGCGG | 1680 |
| CCTAACGGAG | TCATCTTGGA | CTATGAGATG | AAGTACTTTG | AGAAGAGTAA | AGGCATCGCC | 1740 |
| TCCACTGTCA | CCAGCCAGAA | GAACTCTGTA | CAACTGGACG | GACTGCAGCC | CGACGCCCGC | 1800 |
| TATGTAGTTC | AGGTCCGGGC | TCGCACAGTA | GCAGGTTACG | GACAGTATAG | CCGCCCAGCT | 1860 |
| GAGTTTGAGA | CCACGAGTGA | AAGAGGCTCA | GGGGCCCAGC | AGCTTCAAGA | GCAGCTTCCC | 1920 |
| CTAATTGTGG | GATCCACCGT | AGCTGGCTTT | GTCTTCATGG | TGGTCGTCGT | GGTCATTGCT | 1980 |
| CTTGTCTGCC | TCAGGAAGCA | GCGCCAGGGC | CCTGATGCAG | AATACACGGA | GAAGTTGCAG | 2040 |
| CAATACGTTG | CCCCCAGGAT | GAAAGTTTAC | ATTGACCCCT | TACCTACGA | GGATCCCAAT | 2100 |
| GAGGCCGTCC | GAGAGTTCGC | CAAGGAGATC | GATGTGTCCT | GCGTCAAGAT | CGAGGAGGTG | 2160 |
| ATTGGAGCTG | GGGAGTTTGG | GGAAGTGTGC | CGGGGTCGGC | TGAAACTGCC | CGGCCGCCGG | 2220 |
| GAGGTGTTCG | TGGCCATCAA | GACACTGAAG | GTGGGATACA | CGGAGAGGCA | GCGGCGGGAC | 2280 |

| | | | | | | |
|---|---|---|---|---|---|---|
| TTCCTGAGTG | AGGCTTCCAT | CATGGGTCAA | TTTGACCATC | CAAATATAAT | CCGTCTAGAG | 2340 |
| GGCGTGGTCA | CCAAAAGTCG | TCCAGTCATG | ATCCTCACTG | AGTTCATGGA | GAACTGTGCC | 2400 |
| CTGGACTCCT | TCCTACGGCT | CAATGACGGG | CAGTTCACAG | TCATCCAGCT | TGTGGGCATG | 2460 |
| TTGCGTGGCA | TTGCTGCCGG | CATGAAGTAC | TTGTCTGAGA | TGAACTACGT | GCACCGTGAC | 2520 |
| CTCGCTGCCC | GCAACATCCT | TGTCAACAGT | AACTGGTCT | GCAAAGTATC | TGACTTTGGG | 2580 |
| CTCTCCCGCT | TCCTGGAGGA | CGACCCCTCA | GACCCCACCT | ACACCAGCTC | CCTGGGTGGG | 2640 |
| AAGATCCCTA | TCCGTTGGAC | CGCCCCAGAG | GCCATAGACT | ATCGGAAGTT | CACGTCTGCC | 2700 |
| AGCGATGTCT | GGAGCTACGG | GATCGTCATG | TGGGAGGTCA | TGAGCTACGG | AGAGCGACCA | 2760 |
| TACTGGGACA | TGAGCAACCA | GGATGTCATC | AATGCCGTAG | AGCAAGACTA | TCGGTTACCA | 2820 |
| CCCCCCATGG | ACTGCCCAGC | GGCGCTGCAC | CAGCTCATGC | TGGACTGTTG | GGTGCGGGAC | 2880 |
| CGGAACCTCA | GGCCCAAGTT | CTCCCAAATC | GTCAACACGC | TAGACAAGCT | TATCCGCAAT | 2940 |
| GCTGCCAGCC | TCAAGGTCAT | CGCCAGTGCC | CCATCTGGCA | TGTCCCAGCC | CCTCCTAGAC | 3000 |
| CGCACGGTCC | CAGATTATAC | GACCTTCACG | ACGGTGGGCG | ACTGGCTAGA | TGCCATCAAG | 3060 |
| ATGGGGAGGT | ATAAAGAGAG | CTTCGTCGGT | GCGGGTTTTG | CCTCCTTTGA | CCTGGTGGCC | 3120 |
| CAGATGACTG | CAGAAGATCT | GCTAAGGATC | GGGGTCACTT | TGGCCGGCCA | CCAGAAGAAG | 3180 |
| ATCCTCAGCA | GTATCCAGGA | CATGCGGCTG | CAGATGAACC | AGACACTGCC | CGTGCAGGTC | 3240 |
| TGACGCTCAG | CTCCAGCGAG | GGGCGTGGCC | CCCGGGACT | GCACAAGGAT | TCTGACCAGC | 3300 |
| CAGCTGGACT | TTTGGATACC | TGGCCTTTGG | CTGTGGCCCA | GAAGACAGAA | GTTCGGGGGA | 3360 |
| GAACCCTAGC | TGTGACTTCT | CCAAGCCTGT | GCTCCCTCCC | AGGAAGTGTG | CCCCAAACCT | 3420 |
| CTTCATATTG | AAGATGGATT | AGAAGAGGGG | GTGATATCCC | CTCCCCAGAT | GCCTCAGGGC | 3480 |
| CCAGGCCTGC | CTGCTCTCCA | GTCGGGGATC | TTCACAACTC | AGATTTGGTT | GTGCTTCAGT | 3540 |
| AGTGGAGGTC | CTGGTAGGGT | CGGGTGGGGA | TAAGCCTGGG | TTCTTCAGGC | CCCAGCCCTG | 3600 |
| GCAGGGGTCT | GACCCCAGCA | GGTAAGCAGA | GAGTACTCCC | TCCCCAGGAA | GTGGAGGAGG | 3660 |
| GGACTCTGGG | AATGGGGAAA | TATGGTGCCC | CATCCTGAAG | CCAGCTGGTA | CCTCCAGTTT | 3720 |
| GCACAGGGAC | TTGTTGGGGG | CTGAGGGCCC | TGCCTACCCT | TGGTGCTGTC | ATAAAAGGGC | 3780 |
| AGGCGGGAGC | GGGCTGAGAA | ACAGCCTGTG | CCTCCCAGAG | ACTGACTCAG | AGAGCCAGAG | 3840 |
| ACGTGTGTGT | GTGTGTGTGT | GTGTGTGTGT | GTGTGTGTGT | GTGTGTGAAA | GACGGGGGTG | 3900 |
| GGGTATGTAT | GCGTGTGTTG | TGCACATGCT | TGCCTGCACA | GAGAGCATGA | GTGTGTACAA | 3960 |
| GCTTAGCCCT | GTGCCCTGTA | GTGGGGCCAG | CTGGGCAGAC | AGCGAAATAA | AAGGCAATAA | 4020 |
| GTTGAAA | | | | | | 4027 |

( 2 ) INFORMATION FOR SEQ ID NO:4:

( i ) SEQUENCE CHARACTERISTICS:
        ( A ) LENGTH: 4027 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: rat
        ( F ) TISSUE TYPE: skeletal muscle myoblast
        ( H ) CELL LINE: L6

( i x ) FEATURE:
        ( A ) NAME/KEY: CDS
        ( B ) LOCATION: 262..3243
        ( C ) IDENTIFICATION METHOD: by similarity to some other pattern ( x i ) SEQUENCE DESCRIPTION: SEQ ID NO:4:

```
GAAAAATGAA GATCTATACC GACAGCAGAT CAGTGGCTGC CTGGGGCAAA GTTGGAGGGA                60

CATGTTATTT TGATTGTGAT GACATAATAC ATGCAAACAC GGCTAATCCT CTCAAAGCAT               120

ACACTTATAC ATGTGCAGCT TGGTATACAT AAATTATCCA TTACAAAACT ATGAGAAAGC               180

TATCACCACT ATGAAGCACC ACTCACAGTA TGTGAATCTC CACCCCCCTT CCACTGCTGA               240

GACACAGAAA TCCTAGACTG G ATG GAG AAC CCC TAC GTT GGG CGA GCG AGA                 291
              Met Glu Asn Pro Tyr Val Gly Arg Ala Arg
                1               5                  10

GCA GCA GCG GAG CGA GCA GCG GCA GAA GCC ACG AAT TCA CTA TCG ATC                 339
Ala Ala Ala Glu Arg Ala Ala Ala Glu Ala Thr Asn Ser Leu Ser Ile
              15                  20                  25

CTG GTT CGG CCC ACC TCT GAA GGT TCC AGA ATC GAT AGT GAA TTC GTG                 387
Leu Val Arg Pro Thr Ser Glu Gly Ser Arg Ile Asp Ser Glu Phe Val
          30                  35                  40

GAG CTG GCA TGG ACA TCT CAT CCA GAG AGT GGG TGG GAA GAA GTG AGC                 435
Glu Leu Ala Trp Thr Ser His Pro Glu Ser Gly Trp Glu Glu Val Ser
      45                  50                  55

GCC TAC GAT GAA GCC ATG AAT CCT ATC CGC ACG TAT CAG GTG TGT AAC                 483
Ala Tyr Asp Glu Ala Met Asn Pro Ile Arg Thr Tyr Gln Val Cys Asn
  60                  65                  70

GTG CGC GAG TCC AGC CAG AAC AAC TGG CTG CGG ACC GGT TTC ATC TGG                 531
Val Arg Glu Ser Ser Gln Asn Asn Trp Leu Arg Thr Gly Phe Ile Trp
75                  80                  85                  90

CGG CGG GAA GTC CAG CGC GTC TAC GTG GAG CTG AAG TTT ACC GTG AGA                 579
Arg Arg Glu Val Gln Arg Val Tyr Val Glu Leu Lys Phe Thr Val Arg
              95                 100                 105

GAT TGC AAC AGC ATC CCC AAC ATC CCT GGC TCC TGC AAG GAA ACC TTC                 627
Asp Cys Asn Ser Ile Pro Asn Ile Pro Gly Ser Cys Lys Glu Thr Phe
         110                 115                 120

AAC CTT TTT TAC TAC GAG GCT GAT AGC GAT GTG GCG TCA GCC TCC TCT                 675
Asn Leu Phe Tyr Tyr Glu Ala Asp Ser Asp Val Ala Ser Ala Ser Ser
     125                 130                 135

CCC TTC TGG ATG GAG AAC CCC TAC GTG AAA GTG GAC ACC ATT GCG CCA                 723
Pro Phe Trp Met Glu Asn Pro Tyr Val Lys Val Asp Thr Ile Ala Pro
    140                 145                 150

GAT GAG AGC TTC TCG CGG CTA GAC GCT GGG CGC GTT AAC ACC AAA GTG                 771
Asp Glu Ser Phe Ser Arg Leu Asp Ala Gly Arg Val Asn Thr Lys Val
155                 160                 165                 170

CGC AGC TTC GGG CCG CTT TCC AAA GCC GGC TTC TAC TTG GCC TTC CAG                 819
Arg Ser Phe Gly Pro Leu Ser Lys Ala Gly Phe Tyr Leu Ala Phe Gln
                175                 180                 185

GAC CAG GGT GCC TGC ATG TCA CTC ATC TCT GTG CGC GCC TTC TAC AAG                 867
Asp Gln Gly Ala Cys Met Ser Leu Ile Ser Val Arg Ala Phe Tyr Lys
            190                 195                 200

AAG TGT GCA TCC ACC ACT GCA GGC TTC GCA CTC TTC CCC GAG ACC CTC                 915
Lys Cys Ala Ser Thr Thr Ala Gly Phe Ala Leu Phe Pro Glu Thr Leu
        205                 210                 215

ACG GGG GCT GAG CCC ACT TCG CTG GTC ATT GCC CCT GGC ACC TGC ATC                 963
Thr Gly Ala Glu Pro Thr Ser Leu Val Ile Ala Pro Gly Thr Cys Ile
    220                 225                 230

GCT AAC GCT GTG GAG GTG TCT GTA CCG CTC AAG CTC TAC TGC AAT GGC                1011
Ala Asn Ala Val Glu Val Ser Val Pro Leu Lys Leu Tyr Cys Asn Gly
235                 240                 245                 250

GAC GGG GAG TGG ATG GTG CCC GTT GGT GCC TGC ACC TGC GCT ACT GGC                1059
Asp Gly Glu Trp Met Val Pro Val Gly Ala Cys Thr Cys Ala Thr Gly
                255                 260                 265

CAT GAG CCA GCC GCC AAG GAG ACC CAG TGC CGC GCC TGT CCC CCT GGG                1107
```

```
His Glu Pro Ala Ala Lys Glu Thr Gln Cys Arg Ala Cys Pro Pro Gly
        270                 275                 280

AGC TAC AAG GCA AAG CAA GGA GAG GGG CCC TGC CTC CCC TGT CCC CCC    1155
Ser Tyr Lys Ala Lys Gln Gly Glu Gly Pro Cys Leu Pro Cys Pro Pro
        285                 290                 295

AAT AGC CGC ACC ACC TCG CCG GCT GCC AGC ATC TGC ACC TGT CAC AAT    1203
Asn Ser Arg Thr Thr Ser Pro Ala Ala Ser Ile Cys Thr Cys His Asn
        300                 305                 310

AAT TTC TAC CGC GCA GAC TCA GAC ACA GCG GAC AGC GCC TGC ACC ACG    1251
Asn Phe Tyr Arg Ala Asp Ser Asp Thr Ala Asp Ser Ala Cys Thr Thr
315                 320                 325                 330

GTG CCG TCT CCC CCC CGG GGT GTG ATC TCC AAT GTG AAT GAG ACC TCG    1299
Val Pro Ser Pro Pro Arg Gly Val Ile Ser Asn Val Asn Glu Thr Ser
                335                 340                 345

CTG ATC CTC GAG TGG AGT GAG CCC CGG GAC CTT GGC GGA CGA GAT GAC    1347
Leu Ile Leu Glu Trp Ser Glu Pro Arg Asp Leu Gly Gly Arg Asp Asp
            350                 355                 360

CTC CTT TAT AAT GTT ATC TGT AAG AAG TGC CGT GGC AGC TCT GGG GCT    1395
Leu Leu Tyr Asn Val Ile Cys Lys Lys Cys Arg Gly Ser Ser Gly Ala
        365                 370                 375

GGA GGT CCG GCG ACC TGT TCA CGC TGT GAT GAC AAC GTG GAG TTC GAG    1443
Gly Gly Pro Ala Thr Cys Ser Arg Cys Asp Asp Asn Val Glu Phe Glu
380                 385                 390

CCC CGA CAG CTG GGC CTG ACC GAG CGC CGG GTC CAC ATC AGC CAC CTG    1491
Pro Arg Gln Leu Gly Leu Thr Glu Arg Arg Val His Ile Ser His Leu
395                 400                 405                 410

TTG GCC CAC ACC CGC TAC ACC TTT GAG GTG CAG GCT GTC AAC GGC GTC    1539
Leu Ala His Thr Arg Tyr Thr Phe Glu Val Gln Ala Val Asn Gly Val
                415                 420                 425

TCT GGC AAA AGC CCT TTG CCG CCC CGC TAT GCA GCT GTG AAT ATC ACC    1587
Ser Gly Lys Ser Pro Leu Pro Pro Arg Tyr Ala Ala Val Asn Ile Thr
            430                 435                 440

ACC AAC CAG GCC GCC CCA TCA GAA GTG CCT ACG CTC CAC TTG CAC AGC    1635
Thr Asn Gln Ala Ala Pro Ser Glu Val Pro Thr Leu His Leu His Ser
        445                 450                 455

AGT TCA GGG AGC AGC CTG ACC CTG TCC TGG GCA CCC CCG GAG CGG CCT    1683
Ser Ser Gly Ser Ser Leu Thr Leu Ser Trp Ala Pro Pro Glu Arg Pro
460                 465                 470

AAC GGA GTC ATC TTG GAC TAT GAG ATG AAG TAC TTT GAG AAG AGT AAA    1731
Asn Gly Val Ile Leu Asp Tyr Glu Met Lys Tyr Phe Glu Lys Ser Lys
475                 480                 485                 490

GGC ATC GCC TCC ACT GTC ACC AGC CAG AAG AAC TCT GTA CAA CTG GAC    1779
Gly Ile Ala Ser Thr Val Thr Ser Gln Lys Asn Ser Val Gln Leu Asp
                495                 500                 505

GGA CTG CAG CCC GAC GCC CGC TAT GTA GTT CAG GTC CGG GCT CGC ACA    1827
Gly Leu Gln Pro Asp Ala Arg Tyr Val Val Gln Val Arg Ala Arg Thr
            510                 515                 520

GTA GCA GGT TAC GGA CAG TAT AGC CGC CCA GCT GAG TTT GAG ACC ACG    1875
Val Ala Gly Tyr Gly Gln Tyr Ser Arg Pro Ala Glu Phe Glu Thr Thr
        525                 530                 535

AGT GAA AGA GGC TCA GGG GCC CAG CAG CTT CAA GAG CAG CTT CCC CTA    1923
Ser Glu Arg Gly Ser Gly Ala Gln Gln Leu Gln Glu Gln Leu Pro Leu
540                 545                 550

ATT GTG GGA TCC ACC GTA GCT GGC TTT GTC TTC ATG GTG GTC GTC GTG    1971
Ile Val Gly Ser Thr Val Ala Gly Phe Val Phe Met Val Val Val Val
555                 560                 565                 570

GTC ATT GCT CTT GTC TGC CTC AGG AAG CAG CGC CAG GGC CCT GAT GCA    2019
Val Ile Ala Leu Val Cys Leu Arg Lys Gln Arg Gln Gly Pro Asp Ala
                575                 580                 585

GAA TAC ACG GAG AAG TTG CAG CAA TAC GTT GCC CCC AGG ATG AAA GTT    2067
```

|  |  |  |  |  |  |  |  |  |  |  |  |  |  |  |  |
|---|---|---|---|---|---|---|---|---|---|---|---|---|---|---|---|
| Glu | Tyr | Thr | Glu | Lys | Leu | Gln | Gln | Tyr | Val | Ala | Pro | Arg | Met | Lys | Val |
|  |  |  | 590 |  |  |  | 595 |  |  |  |  |  | 600 |  |  |

| TAC | ATT | GAC | CCC | TTT | ACC | TAC | GAG | GAT | CCC | AAT | GAG | GCC | GTC | CGA | GAG | 2115 |
|---|---|---|---|---|---|---|---|---|---|---|---|---|---|---|---|---|
| Tyr | Ile | Asp | Pro | Phe | Thr | Tyr | Glu | Asp | Pro | Asn | Glu | Ala | Val | Arg | Glu |  |
|  |  | 605 |  |  |  | 610 |  |  |  |  | 615 |  |  |  |  |  |

| TTC | GCC | AAG | GAG | ATC | GAT | GTG | TCC | TGC | GTC | AAG | ATC | GAG | GAG | GTG | ATT | 2163 |
|---|---|---|---|---|---|---|---|---|---|---|---|---|---|---|---|---|
| Phe | Ala | Lys | Glu | Ile | Asp | Val | Ser | Cys | Val | Lys | Ile | Glu | Glu | Val | Ile |  |
|  | 620 |  |  |  |  | 625 |  |  |  |  | 630 |  |  |  |  |  |

| GGA | GCT | GGG | GAG | TTT | GGG | GAA | GTG | TGC | CGG | GGT | CGG | CTG | AAA | CTG | CCC | 2211 |
|---|---|---|---|---|---|---|---|---|---|---|---|---|---|---|---|---|
| Gly | Ala | Gly | Glu | Phe | Gly | Glu | Val | Cys | Arg | Gly | Arg | Leu | Lys | Leu | Pro |  |
| 635 |  |  |  | 640 |  |  |  |  | 645 |  |  |  |  | 650 |  |  |

| GGC | CGC | CGG | GAG | GTG | TTC | GTG | GCC | ATC | AAG | ACA | CTG | AAG | GTG | GGA | TAC | 2259 |
|---|---|---|---|---|---|---|---|---|---|---|---|---|---|---|---|---|
| Gly | Arg | Arg | Glu | Val | Phe | Val | Ala | Ile | Lys | Thr | Leu | Lys | Val | Gly | Tyr |  |
|  |  |  |  | 655 |  |  |  |  | 660 |  |  |  |  | 665 |  |  |

| ACG | GAG | AGG | CAG | CGG | CGG | GAC | TTC | CTG | AGT | GAG | GCT | TCC | ATC | ATG | GGT | 2307 |
|---|---|---|---|---|---|---|---|---|---|---|---|---|---|---|---|---|
| Thr | Glu | Arg | Gln | Arg | Arg | Asp | Phe | Leu | Ser | Glu | Ala | Ser | Ile | Met | Gly |  |
|  |  |  | 670 |  |  |  |  | 675 |  |  |  |  | 680 |  |  |  |

| CAA | TTT | GAC | CAT | CCA | AAT | ATA | ATC | CGT | CTA | GAG | GGC | GTG | GTC | ACC | AAA | 2355 |
|---|---|---|---|---|---|---|---|---|---|---|---|---|---|---|---|---|
| Gln | Phe | Asp | His | Pro | Asn | Ile | Ile | Arg | Leu | Glu | Gly | Val | Val | Thr | Lys |  |
|  |  | 685 |  |  |  |  | 690 |  |  |  |  | 695 |  |  |  |  |

| AGT | CGT | CCA | GTC | ATG | ATC | CTC | ACT | GAG | TTC | ATG | GAG | AAC | TGT | GCC | CTG | 2403 |
|---|---|---|---|---|---|---|---|---|---|---|---|---|---|---|---|---|
| Ser | Arg | Pro | Val | Met | Ile | Leu | Thr | Glu | Phe | Met | Glu | Asn | Cys | Ala | Leu |  |
|  | 700 |  |  |  |  | 705 |  |  |  |  | 710 |  |  |  |  |  |

| GAC | TCC | TTC | CTA | CGG | CTC | AAT | GAC | GGG | CAG | TTC | ACA | GTC | ATC | CAG | CTT | 2451 |
|---|---|---|---|---|---|---|---|---|---|---|---|---|---|---|---|---|
| Asp | Ser | Phe | Leu | Arg | Leu | Asn | Asp | Gly | Gln | Phe | Thr | Val | Ile | Gln | Leu |  |
| 715 |  |  |  |  | 720 |  |  |  |  | 725 |  |  |  |  | 730 |  |

| GTG | GGC | ATG | TTG | CGT | GGC | ATT | GCT | GCC | GGC | ATG | AAG | TAC | TTG | TCT | GAG | 2499 |
|---|---|---|---|---|---|---|---|---|---|---|---|---|---|---|---|---|
| Val | Gly | Met | Leu | Arg | Gly | Ile | Ala | Ala | Gly | Met | Lys | Tyr | Leu | Ser | Glu |  |
|  |  |  |  | 735 |  |  |  |  | 740 |  |  |  |  | 745 |  |  |

| ATG | AAC | TAC | GTG | CAC | CGT | GAC | CTC | GCT | GCC | CGC | AAC | ATC | CTT | GTC | AAC | 2547 |
|---|---|---|---|---|---|---|---|---|---|---|---|---|---|---|---|---|
| Met | Asn | Tyr | Val | His | Arg | Asp | Leu | Ala | Ala | Arg | Asn | Ile | Leu | Val | Asn |  |
|  |  |  | 750 |  |  |  |  | 755 |  |  |  |  | 760 |  |  |  |

| AGT | AAC | TTG | GTC | TGC | AAA | GTA | TCT | GAC | TTT | GGG | CTC | TCC | CGC | TTC | CTG | 2595 |
|---|---|---|---|---|---|---|---|---|---|---|---|---|---|---|---|---|
| Ser | Asn | Leu | Val | Cys | Lys | Val | Ser | Asp | Phe | Gly | Leu | Ser | Arg | Phe | Leu |  |
|  |  | 765 |  |  |  |  | 770 |  |  |  |  | 775 |  |  |  |  |

| GAG | GAC | GAC | CCC | TCA | GAC | CCC | ACC | TAC | ACC | AGC | TCC | CTG | GGT | GGG | AAG | 2643 |
|---|---|---|---|---|---|---|---|---|---|---|---|---|---|---|---|---|
| Glu | Asp | Asp | Pro | Ser | Asp | Pro | Thr | Tyr | Thr | Ser | Ser | Leu | Gly | Gly | Lys |  |
| 780 |  |  |  |  | 785 |  |  |  |  | 790 |  |  |  |  |  |  |

| ATC | CCT | ATC | CGT | TGG | ACC | GCC | CCA | GAG | GCC | ATA | GAC | TAT | CGG | AAG | TTC | 2691 |
|---|---|---|---|---|---|---|---|---|---|---|---|---|---|---|---|---|
| Ile | Pro | Ile | Arg | Trp | Thr | Ala | Pro | Glu | Ala | Ile | Asp | Tyr | Arg | Lys | Phe |  |
| 795 |  |  |  |  | 800 |  |  |  |  | 805 |  |  |  |  | 810 |  |

| ACG | TCT | GCC | AGC | GAT | GTC | TGG | AGC | TAC | GGG | ATC | GTC | ATG | TGG | GAG | GTC | 2739 |
|---|---|---|---|---|---|---|---|---|---|---|---|---|---|---|---|---|
| Thr | Ser | Ala | Ser | Asp | Val | Trp | Ser | Tyr | Gly | Ile | Val | Met | Trp | Glu | Val |  |
|  |  |  |  | 815 |  |  |  |  | 820 |  |  |  |  | 825 |  |  |

| ATG | AGC | TAC | GGA | GAG | CGA | CCA | TAC | TGG | GAC | ATG | AGC | AAC | CAG | GAT | GTC | 2787 |
|---|---|---|---|---|---|---|---|---|---|---|---|---|---|---|---|---|
| Met | Ser | Tyr | Gly | Glu | Arg | Pro | Tyr | Trp | Asp | Met | Ser | Asn | Gln | Asp | Val |  |
|  |  |  | 830 |  |  |  |  | 835 |  |  |  |  | 840 |  |  |  |

| ATC | AAT | GCC | GTA | GAG | CAA | GAC | TAT | CGG | TTA | CCA | CCC | CCC | ATG | GAC | TGC | 2835 |
|---|---|---|---|---|---|---|---|---|---|---|---|---|---|---|---|---|
| Ile | Asn | Ala | Val | Glu | Gln | Asp | Tyr | Arg | Leu | Pro | Pro | Pro | Met | Asp | Cys |  |
|  |  | 845 |  |  |  |  | 850 |  |  |  |  | 855 |  |  |  |  |

| CCA | GCG | GCG | CTG | CAC | CAG | CTC | ATG | CTG | GAC | TGT | TGG | GTG | CGG | GAC | CGG | 2883 |
|---|---|---|---|---|---|---|---|---|---|---|---|---|---|---|---|---|
| Pro | Ala | Ala | Leu | His | Gln | Leu | Met | Leu | Asp | Cys | Trp | Val | Arg | Asp | Arg |  |
| 860 |  |  |  |  | 865 |  |  |  |  | 870 |  |  |  |  |  |  |

| AAC | CTC | AGG | CCC | AAG | TTC | TCC | CAA | ATC | GTC | AAC | ACG | CTA | GAC | AAG | CTT | 2931 |
|---|---|---|---|---|---|---|---|---|---|---|---|---|---|---|---|---|
| Asn | Leu | Arg | Pro | Lys | Phe | Ser | Gln | Ile | Val | Asn | Thr | Leu | Asp | Lys | Leu |  |
| 875 |  |  |  | 880 |  |  |  |  | 885 |  |  |  |  | 890 |  |  |

| ATC | CGC | AAT | GCT | GCC | AGC | CTC | AAG | GTC | ATC | GCC | AGT | GCC | CCA | TCT | GGC | 2979 |
|---|---|---|---|---|---|---|---|---|---|---|---|---|---|---|---|---|
| Ile | Arg | Asn | Ala | Ala | Ser | Leu | Lys | Val | Ile | Ala | Ser | Ala | Pro | Ser | Gly |  |
|  |  |  |  | 895 |  |  |  |  | 900 |  |  |  |  | 905 |  |  |

| ATG | TCC | CAG | CCC | CTC | CTA | GAC | CGC | ACG | GTC | CCA | GAT | TAT | ACG | ACC | TTC | 3027 |
|---|---|---|---|---|---|---|---|---|---|---|---|---|---|---|---|---|

|     |     |     |     |     |     |     |     |     |     |     |     |     |     |     |      |
|-----|-----|-----|-----|-----|-----|-----|-----|-----|-----|-----|-----|-----|-----|-----|------|
| Met | Ser | Gln | Pro<br>910 | Leu | Leu | Asp | Arg | Thr<br>915 | Val | Pro | Asp | Tyr | Thr<br>920 | Phe |      |
| ACG | ACG | GTG | GGC | GAC | TGG | CTA | GAT | GCC | ATC | AAG | ATG | GGG | AGG | TAT | AAA | 3075 |
| Thr | Thr | Val<br>925 | Gly | Asp | Trp | Leu | Asp<br>930 | Ala | Ile | Lys | Met | Gly<br>935 | Arg | Tyr | Lys |      |
| GAG | AGC | TTC | GTC | GGT | GCG | GGT | TTT | GCC | TCC | TTT | GAC | CTG | GTG | GCC | CAG | 3123 |
| Glu | Ser<br>940 | Phe | Val | Gly | Ala | Gly<br>945 | Phe | Ala | Ser | Phe | Asp<br>950 | Leu | Val | Ala | Gln |      |
| ATG | ACT | GCA | GAA | GAT | CTG | CTA | AGG | ATC | GGG | GTC | ACT | TTG | GCC | GGC | CAC | 3171 |
| Met<br>955 | Thr | Ala | Glu | Asp | Leu<br>960 | Leu | Arg | Ile | Gly | Val<br>965 | Thr | Leu | Ala | Gly | His<br>970 |      |
| CAG | AAG | AAG | ATC | CTC | AGC | AGT | ATC | CAG | GAC | ATG | CGG | CTG | CAG | ATG | AAC | 3219 |
| Gln | Lys | Lys | Ile | Leu<br>975 | Ser | Ser | Ile | Gln | Asp<br>980 | Met | Arg | Leu | Gln | Met<br>985 | Asn |      |
| CAG | ACA | CTG | CCC | GTG | CAG | GTC | TGACGCTCAG | CTCCAGCGAG | GGGCGTGGCC |     |     |     |     |     |     | 3270 |
| Gln | Thr | Leu | Pro<br>990 | Val | Gln | Val |     |     |     |     |     |     |     |     |     |      |

| | | | | | |
|---|---|---|---|---|---|
| CCCCGGGACT | GCACAAGGAT | TCTGACCAGC | CAGCTGGACT | TTTGGATACC | TGGCCTTTGG | 3330 |
| CTGTGGCCCA | GAAGACAGAA | GTTCGGGGGA | GAACCCTAGC | TGTGACTTCT | CCAAGCCTGT | 3390 |
| GCTCCCTCCC | AGGAAGTGTG | CCCCAAACCT | CTTCATATTG | AAGATGGATT | AGAAGAGGGG | 3450 |
| GTGATATCCC | CTCCCCAGAT | GCCTCAGGGC | CCAGGCCTGC | CTGCTCTCCA | GTCGGGGATC | 3510 |
| TTCACAACTC | AGATTTGGTT | GTGCTTCAGT | AGTGGAGGTC | CTGGTAGGGT | CGGGTGGGGA | 3570 |
| TAAGCCTGGG | TTCTTCAGGC | CCCAGCCCTG | GCAGGGTCT | GACCCCAGCA | GGTAAGCAGA | 3630 |
| GAGTACTCCC | TCCCCAGGAA | GTGGAGGAGG | GGACTCTGGG | AATGGGGAAA | TATGGTGCCC | 3690 |
| CATCCTGAAG | CCAGCTGGTA | CCTCCAGTTT | GCACAGGGAC | TTGTTGGGGG | CTGAGGGCCC | 3750 |
| TGCCTACCCT | TGGTGCTGTC | ATAAAAGGGC | AGGCGGGAGC | GGGCTGAGAA | ACAGCCTGTG | 3810 |
| CCTCCCAGAG | ACTGACTCAG | AGAGCCAGAG | ACGTGTGTGT | GTGTGTGTGT | GTGTGTGTGT | 3870 |
| GTGTGTGTGT | GTGTGTGAAA | GACGGGGGTG | GGGTATGTAT | GCGTGTGTTG | TGCACATGCT | 3930 |
| TGCCTGCACA | GAGAGCATGA | GTGTGTACAA | GCTTAGCCCT | GTGCCCTGTA | GTGGGGCCAG | 3990 |
| CTGGGCAGAC | AGCGAAATAA | AAGGCAATAA | GTTGAAA |     |     | 4027 |

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: rat
        ( F ) TISSUE TYPE: skeletal muscle myoblast
        ( H ) CELL LINE: L6

( x i ) SEQUENCE DESCRIPTION: SEQ ID NO:5:

Val  Ile  Gly  Ala  Gly  Glu  Phe  Gly  Glu  Val  Cys
      1                   5                          10

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v i ) ORIGINAL SOURCE:

(A) ORGANISM: rat
(F) TISSUE TYPE: skeletal muscle myoblast
(H) CELL LINE: L6

(xi) SEQUENCE DESCRIPTION: SEQ ID NO:6:

```
Asn  Ile  Leu  Val  Asn  Ser  Asn  Leu  Val  Cys
 1              5                        10
```

(2) INFORMATION FOR SEQ ID NO:7:

(i) SEQUENCE CHARACTERISTICS:
(A) LENGTH: 5 amino acids
(B) TYPE: amino acid
(D) TOPOLOGY: linear (ii) MOLECULE TYPE: protein (vi) ORIGINAL SOURCE:
(A) ORGANISM: rat
(F) TISSUE TYPE: skeletal muscle myoblast
(H) CELL LINE: L6

(xi) SEQUENCE DESCRIPTION: SEQ ID NO:7:

```
Val  Glu  Gln  Asp  Tyr
 1              5
```

(2) INFORMATION FOR SEQ ID NO:8:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:8:

GTAATACGAC TCACTATAGG GGAGAGCT                      28

(2) INFORMATION FOR SEQ ID NO:9:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:9:

CTCCCCTATA GTGAGTCGTA TTACTGCA                      28

(2) INFORMATION FOR SEQ ID NO:10:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:10:

CTAGTCTATA GTGTCACCTA AATCGTGGGT AC                 32

(2) INFORMATION FOR SEQ ID NO:11:

(i) SEQUENCE CHARACTERISTICS:
(A) LENGTH: 23 base pairs
(B) TYPE: nucleic acid (C) STRANDEDNESS: single
(D) TOPOLOGY: linear (i i) MOLECULE TYPE: DNA (synthetic)

(x i) SEQUENCE DESCRIPTION: SEQ ID NO:11:

CACGATTTAG GTGACACTAT AGA  23

(2) INFORMATION FOR SEQ ID NO:12:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:12:

AATATAGTCG ACCACCATGG AGAACCCCTA CGTTGGGCGA GCGA  44

(2) INFORMATION FOR SEQ ID NO:13:

(i) SEQUENCE CHARACTERISTICS:
(A) LENGTH: 37 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:13:

CGGCGGACTA GTTCAGACCT GCACGGGCAG TGTCTGG  37

(2) INFORMATION FOR SEQ ID NO:14:

(i) SEQUENCE CHARACTERISTICS:
(A) LENGTH: 55 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:14:

GCCGCCACTA GTTCAGTGGT GGTGGTGGTG GTGGACCTGC ACGGGCAGTG TCTGG  55

(2) INFORMATION FOR SEQ ID NO:15:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:15:

CGGCGGACTA GTTCATGAGC CTCTTTCACT CGTGGTCTCA AACT  44

(2) INFORMATION FOR SEQ ID NO:16:

(i) SEQUENCE CHARACTERISTICS:
(A) LENGTH: 62 base pairs
(B) TYPE: nucleic acid
(C) STRANDEDNESS: single
(D) TOPOLOGY: linear (i i) MOLECULE TYPE: DNA (synthetic)

( x i ) SEQUENCE DESCRIPTION: SEQ ID NO:16:

GCCGCCACTA GTTCAGTGGT GGTGGTGGTG GTGTGAGCCT CTTTCACTCG TGGTCTCAAA    60

CT    62

POLYPEPTIDE OF PROTEIN P140 AND DNAS ENCODING IT

SUMMARY

The present invention is related to a novel protein p140 polypeptide which is a key protein involved in the signal transmission system of insulin; method for preparation of it; DNA encoding the said polypeptide; vector comprising the said DNA; host cells transformed with the said vector; antibody against the said polypeptide; pharmaceutical composition containing the said peptide or antibody; method for the prevention and/or treatment of diabetes, which is characterized by tyrosine phosphorylation of the said protein p140 (to be quoted henceforth as phosphorylation in the present detailed specification); agent for the prevention and/or treatment of diabetes, which is characterized by containing a compound which can tyrosine phosphorylate protein p140, as active ingredient and screening methods for the said prevention and/or treatment agent.

BACKGROUND OF INVENTION

Diabetes, an abnormal metabolic disease, is induced by a defect in the mechanism of glucose metabolism.

Under normal conditions, glucose metabolism occurs as follows: carbohydrates, consumed in the form of food, are digested to glucose in the intestines prior to absorption into the circulatory system. Pancreatic β cells respond to an increase in the blood glucose level by secreting insulin, which in turn stimulates the target peripheral tissues (muscles and liver) to decrease the blood glucose level by enhancing tissue absorption of the blood glucose followed by the conversion of glucose to glycogen for storage.

Depending on the causative factors, diabetes is classified into two major categories; insulin dependent diabetes mellitus (IDDM) and non-insulin dependent diabetes mellitus (NIDDM). IDDM (Type I diabetes) is a pathological condition where insulin is not secreted or insufficient even on secretion by pancreatic β cells responding to an increase in the blood glucose level induced by food consumption. It has been known that destruction of β cells of the pancreatic islets induces IDDM. The current therapy employs supplementation of insulin from exogenous sources.

NIDDM (Type II diabetes)is a pathological condition where the feedback mechanism of peripheral tissues is dysfunctional and is ineffective in decreasing the blood glucose level although normal insulin secretion occurs within the living system. In the United States of America, NIDDM is said to be a common disease; 5% of the population exceeding 40 years of age suffer from NIDDM. Causative factors involved in this disease have yet to be elucidated.

RELATED ARTS

Elucidation of the etiology of NIDDM; namely, clarification of the insulin-induced glucose uptake mechanism in peripheral tissue cells is, however, unclear as current knowledge on information transmission mechanism of insulin remains limited and unestablished.

Insulin secreted from the pancreatic islets binds with insulin receptors on the cell membrane of peripheral tissue cells. With regard to post-binding information transmission, the phosphorylase cascade and second messenger theories are the current topics of research.

Briefly, these two theories can be accounted as follows:

Phosphorylase cascade theory:

When insulin binds with the insulin receptor α subunit, the β subunit existing on the inner cell membrane triggers phosphorylation accompanied by activation of the tyrosine kinase site within the receptor. Phosphorylation of substrates by the latter enzyme produces three different proteins. One is composed of 1,235 amino acids and has a molecular weight of 185 kD corresponding to the insulin receptor substrate-1 (IRS-1). On tyrosine phosphorylation of IRS-1, the phosphorylase for phosphatidylinositol, PI1-kinase, binds against and activates the complex. Post-binding events related to information transmission that concerns localization of glucose transporter within the membrane and membrane ruffling have yet to be established. Other than IRS-1, the existence of two protein substrates (Shc and PTP-1C) has been confirmed. However, the follow-up mechanism(s) has not been completely accounted for.

Second messenger theory:

When insulin binds against the insulin receptor, phospholipase C is specifically activated to degrade phosphatidylinositol glycan (PIG) to produce inositolglycan (IG) and diacylglycerol (DAG) by hydrolysis. Although IG has been reported to display various insulin-like effects, the typical glucose uptake effect has yet to be demonstrated.

However, when protein kinase C is activated by DAG, localization of protein kinase C within the cell membrane has been known to be promoted. This implicates that DAG sequentially phosphorylates inner membrane proteins to finally trigger the glucose uptake. However, this implication remains hitherto unclear.

Although the two different schools of thought have hitherto prevailed, initial stages of the post-binding events related to information transmission can only be explained in part by either theory.

According to Copper et al. (1988) the hormone, amylin, is released from β pancreatic cells similar to those that secret insulin when hyperglycemia prevails. Based on their findings that amylin inhibited the action of insulin, they revealed that the hormone might be used as an insulin antagonist. A follow-up report in 1991 indicates that the excessive use of amylin in transgenic mice induces NIDDM. However, the relationship of amylin with insulin information transmission remains hitherto unexplored.

Means to Solve the Problems

The inventors of the present invention focus on the insulin antagonistic properties of amylin. With persistent research activities conducted on the effects of amylin on the insulin information transmission system, the inventors first identified the inhibition site of amylin in regulating the insulin information transmission system and discovered the key proteins, phosphorylated proteins 140 and 70 (pp140 and pp70), related to this phenomenon. The present invention reveals clearly the structures of said proteins (DNA base sequences and amino sequences) and elucidation of their functions to totally complement the hitherto deficiently explained insulin information transmission phenomenon.

DISCLOSURE OF THE INVENTION

Figure 1:
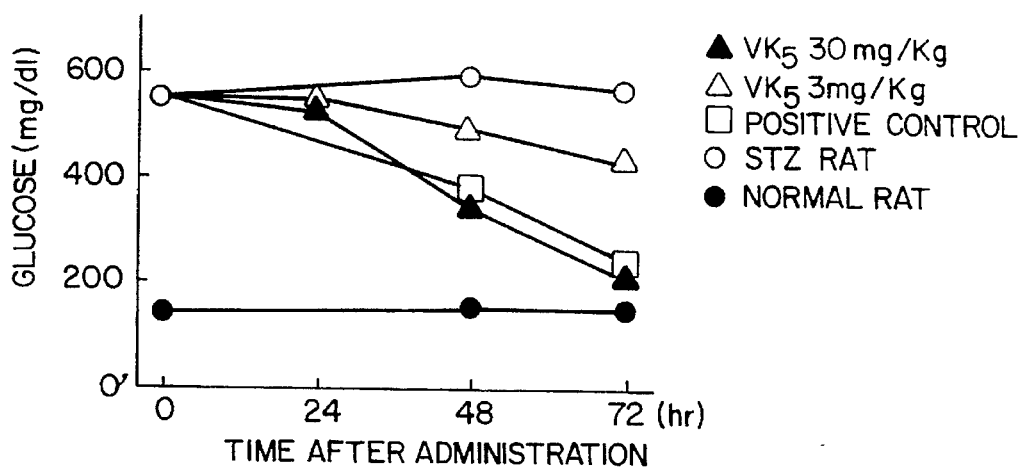
FIG. 1 shows an effects of vitamin $K_5$ ($VK_5$) on blood glucose contents in streptozotocin (STZ)-induced diabetic rats.

The present invention relates to homologues and fragment sequences of the genuine amino acid sequence of the said protein p140 constructed from SEQ ID No. 1 as shown. In addition, DNAs encoding the related polypeptides of the said homologues and fragment sequences are also encompassed in the present invention. Expressed on a more concrete aspect, the said DNAs are those either encoding and/or possessing fragments selectively hybridizing to base sequences illustrated in SEQ ID No.2 and 3.

Furthermore, the present invention is directed to a method for the prevention and/or treatment of diabetes, which is characterized by tyrosine phosphorylation of the said protein p140; agent for the prevention and/or treatment of diabetes, which is characterized by containing a compound which can tyrosine phosphorylate protein p140, as active ingredient and the screening methods of the said prevention and/or treatment agent.

The present invention specifically includes:

(1) polypeptides constructed by amino sequence(s) illustrated in SEQ ID No. 1.

(2) DNAs encoding polypeptides described in (1).

(3) DNAs possessing base sequences illustrated in SEQ ID No. 2.

(4) DNAs possessing base sequences illustrated in SEQ ID No. 3.

(5) Method for the prevention and/or treatment of diabetes, which is characterized by tyrosine phosphorylation of protein p140

(6) Agent for the prevention and/or treatment of diabetes, which is characterized by tyrosine phosphorylation of protein p140

(7) Agent for the prevention and/or treatment of diabetes, which is characterized by containing a compound which can tyrosine phosphorylate protein p140, as active ingredient and (8) Method for the screening of the agent for the prevention and/or treatment of diabetes, which is characterized by using protein p140.

On administering amylin (0.1 mg/kg, i.p., t.i.d.) to healthy rats for 7 days, dramatic decreases occurred in both incidences of insulin receptor population and secreted insulin quantity. These observations were accompanied by decreases in both incidences, of glucose transporter 4 (Glut 4) quantity and synthesized glycogen content (less than 50% decrease compared to that of control group) with a 1.7-fold increase in the blood glucose content. Furthermore, in experiments using L6 cells (ATCC strain No., CRL-1458) of rat skeletal muscle myoblasts, a decreased glucose uptake in the cells was observed with amylin administration.

Next, changes in the insulin-induced tyrosine phosphorylation cascade in skeletal muscle myoblasts treated with amylin were investigated by using the anti-phosphotyrosine antibody with the western blot method. As such, when L6 cells were incubated with insulin in the experiments, tyrosine phosphorylation was enhanced. However, pretreatment with amylin under similar conditions confirmed the presence of two different proteins that were inhibited in phosphorylation. These proteins are henceforth termed as. pp140 and pp70 according to their respective molecular weights. Furthermore, the precursors of these said proteins prior to phosphorylation are henceforth designated as p140 and p70 respectively.

The inventors prepared, isolated and purified the pp140 and pp70 before determining their partial amino acid sequences, On comparing similarities of the said amino acid sequences with previously documented sequences of polypeptides in Swiss Plot Release 2.0, pp70 coincides with the previous known glucose-regulated protein 70. However, the results postulate pp140 as a totally unknown novel protein. As such, inventors of the present invention isolated mRNA of p140 from the rat skeletal muscle myoblasts and constructed the cDNA using the isolated mRNA of p140 before determining the whole base sequence and complete amino acid sequence of the said protein. The results therefore complement the present invention by revealing successfully a completely novel polypeptide and the total DNA chain encoding this polypeptide.

From the above findings, it is understood that amylin may inhibit phosphorylation of p140 and p70 into pp140 and pp70 respectively. In contrast, when amylin is considered to suppress the process from insulin receptor binding to glucose uptake, it suggests that phosphorylation of p140 and p70 to yield pp140 and pp70 may play an important role in the glucose uptake mechanism of cells.

The inventors of the present invention attempted to elucidate the mechanism(s) of action of p140 and p70 accordingly.

When rat skeletal muscle myoblasts (rat L6 cells) were incubated in insulin-supplemented cultures, incidence of a pp140 band on day 3 with pp140 production on day 9 were persistently observed. At about the similar interval (day 3), incidence of Glut 4 was similarly observed with gradual increases in rat L6 cell division. Furthermore, polynucleation of rat skeletal muscle myoblasts was observed on day 7 in the similar culture system with subsequent division to form the muscle cells. In the case of pp70, the cells appeared on day 7 and persisted to register production of the protein until day 14.

However, on examining localization of pp140 within the cells, the protein was found within the microsome membrane (MM) of the cytoplasm in the cell at post-culture 10 min when insulin was added to non-serum treated L6 cells. The pp140 disappeared thereafter. In addition, pp140 was first observed in the cell permeable membrane (PM) at post-culture 1~2 hr. From these findings, pp140 is postulated to have been synthesized in cell cytoplasm immediately after insulin treatment ensued with transfer of this protein to the permeable membrane (PM) 1~2 hr thereafter. Furthermore, when pp70 localization in L6 cells was investigated with a similar experimental approach, pp70 was first located in the MM immediately after initiating the culture, registered a peak phosphorylated quantity at post-culture 10 min and gradually approached non-detectable values at post-culture 3 hr. Moreover, pp70 was also located within the nucleus immediately after initiating the culture, and the protein content gradually increased to register a peak value at post-culture 3 hr. From the above protein localization patterns, pp70 exists in MM in the absence of insulin and this protein is mobilized to the nucleus fraction within 3 hr after insulin treatment.

Based on the above results, pp140 information transmission mechanism may be postulated as follows. In short, when insulin binds to the receptor, the latter is activated by auto-phosphorylation. The information is then subjected to undergo various steps of activation via phosphorylation of protein phosphorylases to subsequently phosphorylate p140 to pp140. The activated pp140 localizes on permeable membrane (PM) surface before p70 is phosphorylated after undergoing various protein phosphorylation processes simultaneously. The phosphorylated pp70 is activated then mobilized to within the nucleus to subsequently trigger biological activities in the Glut 4 expression within the nucleus. Based on this information, Glut 4 produced within the cytoplasm is hence mobilized to localize on the permeable membrane (PM) surface to eventually trigger glucose uptake.

The above information transmission mechanism warrants follow-up experiments to righteously establish concrete evidence of the phenomenon. In any case, it can now be concluded that activation of p140 is an essential step required to induce glucose uptake in cells and subsequent hypoglycemia in the circulatory system.

As such, the present invention is related to method for the prevention and/or treatment of diabetes, especially non-insulin dependent diabetes mellitus (NIDDM), which is characterized by tyrosine phosphorylation of protein p140.

Moreover, the present invention is related to agent for the prevention and/or treatment of diabetes, especially non-insulin dependent diabetes mellitus (NIDDM), which is characterized by tyrosine phosphorylation of protein p140.

In the present invention, method and agent for the prevention and/or treatment of diabetes, which is characterized by tyrosine phosphorylation of protein p140, includes all or whole of the said method and agent for the prevention and/or treatment of diabetes based on the major mechanism of action involving tyrosine phosphorylation of protein p140.

In addition, cells that tyrosine phosphorylate protein p140 are not only confined to skeletal muscle myoblasts (rat L6 cells), but also include all other cells that positively elicit the phosphorylation. All in all, cells that have been confirmed to display the phosphorylation include rat FaO hepatocytes, human A673 muscle cells and HepG2 hepatocytes.

Organs other muscles and liver such as the heart, brain, spleen, lungs, kidneys, testes, placenta and pancreas have repeatedly displayed incidences of p140 mRNA of the present invention. Without being confined merely to muscles and liver, the effects of tyrosine phosphorylation may therefore radiate extensively throughout the living system. From this finding, the said mechanism of action of the present invention is hence not limited to muscle and liver cells, but involves the cardiac, encephalic, splenic, pulmonary, renal testical, placental and pancreatic cells as well.

When the polypeptide of the present invention was compared with amino acid sequences of previously known polypeptides recorded with the Swiss Prot Release 2.0, candidates with a complete whole sequence similar to that of the polypeptide were not identified. Furthermore, no single cDNA of the complete whole polypeptide of the present invention encoding the previously documented nucleotide sequences recorded in the GertBank Release 70 was located. The said peptide of the present invention is hence confirmed to be a completely novel protein.

Additionally, epithelial cell kinase (Eck) with approximately 40% identity was recognized when the results were compared with amino acid sequences of polypeptides previously documented in the Swiss Prot Release 2.0. As such, a novel protein of the present invention was postulated to belong to the Eck family.

In the present invention, a polypeptide of Seq. ID No. 1 in substantially purified form will generally comprise the polypeptide in a production in which more than 90%, e.g. 95%, 98% or 99% of the polypeptide in the production is that of the Seq. ID No. 1.

A polypeptide homologue of Seq. ID No. 1 will be generally at least 70%, preferably at least 80 or 90% and more preferably at least 95% homologous to the polypeptide of Seq. ID No. 1 over a region of at least 20, preferably at least 30, for instance 40, 60 or 100 more contiguous amino acids. Such polypeptide homologues will be referred to below as a polypeptide according to the invention.

Generally, fragments of Seq. ID No. 1 or its homologues will be at least 10, preferably at least 15, for example 20, 25, 30, 40, 50 or 60 amino acids in length, and are also encompassed by the term "a polypeptide according to the invention" as used herein.

A DNA capable of selectively hybridizing to the DNA of Seq. ID No. 2 or 3 will be generally at least 70%, preferably at least 80 or 90% and more preferably at least 95% homologous to the DNA of Seq. ID No. 2 or 3 over a region of at least 20, preferably at least 30, for instance 40, 60 or 100 or more contiguous nucleotides. Such DNA will be encompassed by the term "DNA according to the invention".

Fragments of the DNA of Seq. ID No. 2 or 3 will be at least 10, preferably at least 15, for example 20, 25, 30 or 40 nucleotides in length, and are also encompassed by the term "DNA according to the invention" as used herein.

A further embodiment of the invention provides replication and expression vectors comprising DNA according to the invention. The vectors may be, for example, plasmid, virus or phage vectors provided with an origin of replication, optionally a promoter for the expression of the said DNA and optionally a regulator of the promoter. The vector may contain one or more selectable marker genes, for example an ampicillin resistant gene. The vector may be used in vitro, for example for the production of RNA corresponding to the DNA, or used to transfect or transform a host cell.

A further embodiment of the invention provides host cells transformed or transfected with the vectors for the replication and expression of DNA according to the invention, including the DNAs of SEQ. ID Nos. 2 or 3 or the open reading frame thereof. The cells will be chosen to be compatible with the vector and may for example be bacterial, yeast, insect or mammalian.

A further embodiment of the invention provides a method of producing a polypeptide which comprises culturing host cells of the present invention under conditions effective to express a polypeptide of the invention. Preferably, in addition, such a method is carried out under conditions in which the polypeptide of the invention is expressed and then produced from the host cells.

DNA according to the invention may also be inserted into the vectors described above in an antisense orientation in order to provided for the production of antisense RNA. Antisense RNA may also be produced by synthetic means. Such antisense RNA may be used in a method of controlling the levels of a polypeptide of the invention in a cell.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen. Polyclonal antibodies may also be prepared by conventional means which comprise inoculating a host animal, for example a rat or a rabbit, with a polypeptide of the invention and recovering immune serum.

The present invention also provides pharmaceutical compositions containing a polypeptide of the invention, or an antibody thereof, in association with a pharmaceutically acceptable diluent and/or carrier.

The polypeptide of the present invention includes that in which a part of its amino acid sequence is lacking (e.g., a polypeptide comprised of the only essential sequence for revealing a biological activity in an amino acid sequence shown in SEQ ID No. 1), that in which a part of their amino acid sequence is replaced by other amino acids (e.g., those replaced by an amino acid having a similar property) and that into which other amino acids are added or inserted into a part of their amino acid sequence, as well as those having the amino acid sequence shown in SEQ ID NO. 1.

As known, there are one to six kind codons encoding each amino acid (for example, one codon for Met, and six codons for Leu) are known. Accordingly, the nucleotide sequence of DNA can be changed in order to encode the polypeptide having the same amino acid sequence.

The DNA of the present invention, specified in (2) includes a group of every nucleotide sequences encoding the polypeptides (1) shown in SEQ ID NO. 1 . There is a probability of improving a yield of production of a polypeptide by changing the nucleotide sequence.

The DNA specified in (3) is an embodiment of the DNA in (2), and is the sequence in the natural form.

The DNA in (4) indicates the sequence of the DNA specified in (3) with a non-translational region.

The DNA having the nucleotide sequence shown in SEQ ID NO. 3 may be prepared according to the following methods, that is:

(i) by isolating mRNA from a cell line which produces the polypeptide of the present invention (e.g., rat skeletal muscle myoblasts L6 cell), (ii) by preparing a first strand (single stranded DNA) from mRNA thus obtained, followed by preparing a second strand (double stranded DNA) (synthesis of cDNA), (iii) by inserting cDNA thus obtained into a proper plasmid vector, (iv) by transforming host cells with the recombinant DNA thus obtained (preparation of clDNA library), (v) by random-cloning on a large scale from cDNA library thus obtained, followed by sequencing an average of 300 bases from 5' end of each clone, and (vi) by sequencing the complete length of a clone which has a novel base sequence.

Explained in detail, step (i) may be carried out in accordance with the method of Okayama, H. et al. (described in *Methods in Enzymology*, 154, 3, (1987)) using L6 cells of a rat skeletal muscle myoblasts which have a logarithmic growth phase. Examples of the cells which produce the polypeptide of the present invention are muscle, liver, heart, brain, spleen, lungs, kidneys, testes, placenta or pancreas of a rat or human, and are preferably rat skeletal muscle myoblasts L6 cell (ATCC strain No., CRL-1458), rat liver FaO cell, human muscle A673 cell or human liver HepG2 cell. Steps (ii), (iii) and (iv) are a series of steps for preparing cDNA library, and may be carried out in accordance with the method of Gubler & Hoffman (*Gene*, vol. 25, pp. 263, 1983) with a slight modification. As examples of the plasmid vector used in step (iii), many vectors functioning in an *E. coli* strain (e.g., pBR 322) and in a *Bacillus subtills* (e.g., pUB 110) are known, and pGEM-3Zf(+) (3,199 bp, manufactured by Promega Corp.) which functions in an *E. coli*, may be preferably used. As examples of host used in step (iv), many cells are already known. Any cells may be used, and DH5 competent cells which have been prepared in accordance with the method described in *Gene*, vol. 96, pp. 23, 1990, may be preferably used. The cloning in step (v) may be carried out by methods known per se and the sequencing may be carried out in accordance with the method of Maxam-Gilbert or the dideoxy termination method. The step (vi) may be carried out in accordance with the method described in Molecular Cloning (written by Sambrook, J., Fritsch, E. F. and Maniatis, T., published by Cold Spring Harbor Laboratory Press in 1989).

As the following step, it is necessary to examine whether or not the DNA thus obtained codes correctly produce a protein. The examination requires:

(I) the conversion of the DNA sequence into the amino acid sequence in a possible frame, (II) the confirmation that the DNA thus obtained covers a complete or almost complete length of intact mRNA. This confirmation may be carried out after step (vi) hereinbefore described, and effectively between step (v) and step (vi).

The step (II) may be carried out by Northern analysis.

Once the nucleotide sequences shown in SEQ ID NOs. 2 and 3 are determined, DNA of the present invention may be obtained by chemical synthesis, by PCR method or by hybridization making use of a fragment of DNA of the present invention, as a probe. Furthermore, DNA of the present invention may be obtained in a desired amount by transforming with a vector containing a DNA of the present invention into a proper host, followed by culturing the transformant.

The polypeptides of the present invention (shown in SEQ ID NO. 1) may be prepared by:

(1) isolating and purifying from an organism or a cultured cell, (2) chemically synthesizing, or (3) using a skill of biotechnology, preferably, by the method described in (3).

Examples of an expression system when preparing a polypeptide by using a skill of biotechnology is, for example, the expression system of bacteria, yeast, insect cell and mammalian cell.

For example, the expression in *E. coli* may be carried out by adding the initiation codon (ATG) to the 5' end of a DNA encoding a nucleotide sequence shown in SEQ ID NO. 3, connecting the DNA thus obtained downstream of a proper promoter (e.g., trp promoter, lac promoter, $\lambda p_L$ promoter, T7 promoter etc.), and then inserting it into a vector (e.g., pBR322, pUC18, pUC19 etc.) which functions in an *E. coli* strain to prepare an expression vector. Then, an *E. coli* strain (e.g., *E. coli* DH1 strain, *E. coli* JM109 strain, *E. coli* HB101 strain, etc.) which is transformed with the expression vector thus obtained may be cultured in a proper medium to obtain the desired polypeptide. When a signal peptide of bacteria (e.g., signal peptide of pel B)is utilized, the desired polypeptide may be also secreted in periplasm. Furthermore, a fusion protein with other polypeptide may also be produced easily.

Furthermore, the expression in a mammalian cell may be carried out, for example, by inserting the DNA shown in SEQ ID NO. 3 downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.) to obtain an expression vector, and transforming a proper mammalian cell (e.g., monkey COS-7 cell, Chinese hamster CHO cell, mouse L cell etc.) with the expression vector thus obtained, and then culturing the transformant in a proper medium to get a desired polypeptide in the culture medium. The polypeptide thus obtained may be isolated and purified by conventional biochemical methods.

The protein of the present invention includes the reaction products of phosphorylated and/or sugar-chained protein. In short, the present invention contains p140-bound polysaccharide chains and tyrosine phosphorylated p140 (pp140) found in p140 polypeptides.

EFFECTS OF INVENTION

The protein p140 is postulated to possess the above-mentioned mechanism of action. The protein p140 polypeptide of the present invention can therefore not only improve the hyperglycemic conditions when used alone, but can also be useful in prevention and/or treatment for diabetes, especially non-insulin dependent diabetes mellitus (NIDDM).

Further, polyclonal or monoclonal antibodies against the protein p140 polypeptide of the present invention can be used in the determination of the amount of the said polypeptide in organism, and thereby, may be utilized for the purpose of investigating the relationship between the said polypeptide and diseases, or for the purpose of diagnosing diseases, and the like. Polyclonal and monoclonal antibody thereof may be prepared by conventional methods by using the said polypeptide or the fragment thereof as an antigen.

The DNA of the present invention may be utilized as an important and essential template in preparing the polypeptide of the present invention which is expected to possess various use or for diagnosis of and in the treatment of gene diseases (the treatment of gene defect disease and the treatment by inhibiting expression of the polypeptide by antisense DNA (RNA), and the like). Further, genomic DNA may be isolated by using the DNA of the present invention as a probe. Similarly, it is possible to isolate genes having high homology to the DNA of the present invention in human or those of other species.

Furthermore, the present invention is related to an agent for the prevention and/or treatment of diabetes characterized by containing a compound which can tyrosine phosphorylate protein p140, as active ingredient.

All in all, tyrosine phosphorylated protein p140 products include not only currently confirmed substances that possess the said activities but also all those substances that will be confirmed to possess the said activities henceforth. At present, it is confirmed that the compounds have activity of tyrosine phosphorylation, for example, (1) the benzene or naphthalene derivatives of the formula (I)

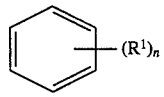
(Ia)

or

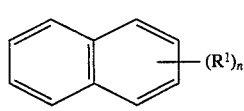
(Ib)

wherein $R^1$ of n species each, independently, is hydrogen atom C1–4 alkyl, hydroxy, amino or $COOR^2$ (in which $R^2$ is hydrogen atom or C1–4 alkyl), n is 1–3 and non-toxic salts thereof and non-toxic acid addition salts thereof, (2) the benzoquinone or naphthoquinone derivatives of the formula (II)

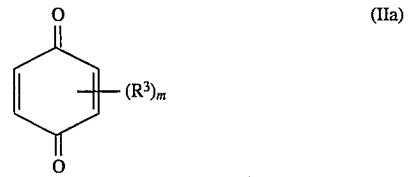
(IIa)

or

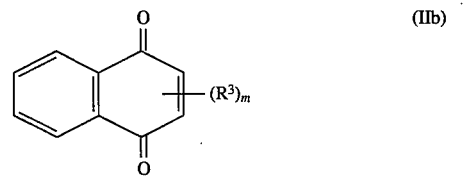
(IIb)

wherein $R^3$ of m species each, independently, is hydrogen atom, C1–12 alkyl, C1–4 alkoxy, C1–4 alkylthio, hydroxy, halogen, phenyl or phenyl substituted by halogen, m is 1–4, (3) the rhodanine or thazolidine derivatives of the formula (III)

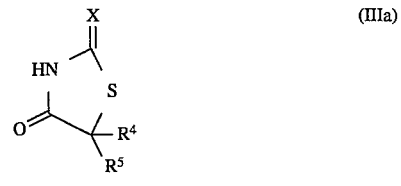
(IIIa)

or

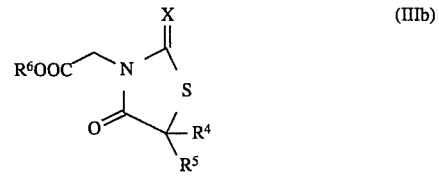
(IIIb)

wherein X is oxygen or sulfur atom, $R^4$ and $R^5$ each, independently, is hydrogen atom, phenyl or phenyl substituted by C1–4 alkyl, C1–8 alkoxy, halogen atom or nitro, or $R^4$ and $R^5$, taken together, represent benzylidene, benzylidene substituted by C1–4 alkyl, C1–8 alkoxy, halogen atom or nitro or p-methylcinnamilidene, $R^6$ is hydrogen atom C1–4 alkyl, and non-toxic salts thereof and non-toxic acid-addition salts thereof.

More concretely, the compounds of the formula (I) include 4-amino-2-hydroxybenzoic acid, 4-amino-1-naphthol, 4-amino-2-naphthol, 1-aminonaphthalene, 1,4-dihydroxynaphthalene, 4-amino-2-methyl-1-naphthol (abbreviated as vitamin $K_5$ hereinafter), 1,4-dihydroxy-2-naphthenic acid, etc.

The compounds of the formula (II) include 2-methyl-1, 4-benzoquinone, 2,6-di-tert-butyl-1,4-benzoquinone, 2,6-dibromo-1,4-benzoquinone, 2,3,4,5-tetrafluoro-1,4-benzoquinone, 1,4-naphthoquinone, 2-methyl-1,4-naphthoquinone (abbreviated as vitamin K3 hereinafter), 2-hydroxy-3-methyl-1,4-naphthoquinone, 2-(3,7-dimethyloctyl)-3-hydroxy-1,4-naphthoqunone, 2-methoxy-3-methyl-1,4-naphthoquinone, 2-hydroxy-1,4-naphthoquinone, 3-(4-chlorophenyl)-2-hydroxy-1,4-naphthoquinone, 2-propylthio- 1,4-naphthoquinone, etc.

The compounds of the formula (III) include 5-phenylrhodanine, 5-phenyl-1,3-thiazodidine-2,4-dione, 5-benzylidenerhodanine, 5-benzylidene-1,3-thiazodidine-2,4-dione, 5,5-diphenylrhodanine, 5,5-diphenyl- 1,3-thiazodidine- 2,4-dione, 5-(4isoamyloxybenzylidene)rhodanine, 5-(4-isoamyloxybenzylidene)-1,3-thiazodidine-2,4-diene, 5-(β-methylcinnamylidene)rhodanine-3-acetic acid, etc., and non-toxic salts thereof and non-toxic acid addition salts thereof.

In the present invention, the appropriate non-toxic salts, for example, are salts of alkali metal (e.g., potassium, sodium etc.), salts of alkaline earth metal (e.g., calcium, magnesium etc.), ammonium salts and, salts of pharmaceutically-acceptable organic amine (e.g., tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

In the present invention, the appropriate acid addition salts include the salts with inorganic acids such as hydrochloric acid, hydrobromic acid, sulfuric acid, phosphoric acid and nitric acid, and the salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

The compound of the formulae (I), (II) and (III) are well known per se, or used as other starting materials may be easily prepared by methods known per se.

As the substances used in the present invention are subjected to tyrosine phosphorylation, these agents not only improve the diabetes-derived hyperglycemic conditions but are also useful for the treatment and/or prevention of diabetes, especially non-insulin dependent diabetes mellitus (NIDDM).

It was confirmed that the toxicity of the various active ingredient and salts thereof of the present invention is very low. Therefore, it may be considered that the various active ingredient and acid-addition salts thereof of the present invention are safe and suitable for pharmaceutical use.

For the above described purpose, the polypeptide, each active ingredient and acid addition salts thereof of the present invention, may be normally administered systemically or partially, usually by oral or parenteral administration.

The doses to be administered are determined depending upon e.g., age, body weight, symptom, the desired therapeutic effect, the route of administration, and the duration of the treatment. In the human adult, the doses per person per dose are generally between 10 μg and 1000 mg, by oral administration, up to several times per day, and between 10 μg and 100 mg, by parenteral administration up to several times per day, or by continuous intravenous administration between 1 and 24 hrs. per day.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, and as injections, liniments or suppositories for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate). The compositions may also comprise, as is normal practice, additional substances other than inert diluents: e.g. lubricating agents (such as magnesium stearate), disintegrating agents (such as cellulose calcium glycolate), stabilizing agents (such as lactose), and agents to assist dissolution (such as glutamic acid, asparaginic acid).

The tablets or pills may, if desired, be coated with a film of gastric or enteric material (such as sugar, gelatin, hydroxypropyl cellulose or hydroxypropylmethyl cellulose phthalate), or be coated with more than two films. Coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (such as purified water, ethanol). Besides inert diluents, such compositions may also comprise adjuvants (such as wetting agents, suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate, citric acid). For preparation of such spray compositions, for example, the methods described in the U.S. Pat. Nos. 2,868,691 or 3,095,355 may be used.

Injections for parenteral administration include sterile aqueous or non-aqueous solutions, suspensions and emulsions. In such compositions, one or more active compound(s) is or are admixed with at least one inert aqueous diluent(s) (such as distilled water for injection, physiological salt solution) or inert non-aqueous diluent(s) (such as propylene glycol, polyethylene glycol, olive oil, ethanol, POLYSORBATE 80 (registered trade mark)).

Injections may comprise additional materials other than inert diluents: e.g. preserving agents, wetting agents, emulsifying agents, dispersing agents, stabilizing agent (such as lactose), and agents to assist dissolution (such as glutamic acid, asparaginic acid).

They may be sterilized for example, by filtration through a bacteria-retaining filter by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by methods known per se.

EXAMPLES

The following examples are to illustrate, but not limit, the present invention.

EXAMPLE 1

Purification method of pp140

By employing cell trays (225 cm$^2$), rat L6 cells were incubated at 37° C. for 7~10 days in 5% $CO_2$ atmosphere. Culture media were replaced at 3-day intervals with the Dulbecco's modified Eagle's medium (containing 10% bovine fetal serum (BFS)). Two hours after treating the muscle cells developed from skeletal muscle myoblasts with serum-free medium, 500 μM vanadic acid (vanadate) was added to the culture and allowed to incubate further for 10 min. Cells were then suspended in Tris buffer (400 μM vanadate with protease inhibitor), lysed and centrifuged prior to isolating the supernatant.

The supernatant was adjusted with octa (ethylene glycol) ether ($C_{12}E_8$) to a final concentration of 0.1% before filtration through a millipore membrane. Protein G sepharose gel bound with anti-phosphotyrosine antibodies was filled with the filtered sample. The tyrosine phosphorylated protein (pp140) adsorbed to the gel. After rinsing the column with 25 mM Tris buffer, pp140 was eluted with 10 mM phenylphosphate. The eluate was concentrated with Centricon 30 prior to precipitating pp140 by the acetone precipitation method.

EXAMPLE 2

Tyrosine phosphorylation of p140 in various tissues

Using the Dubecco's modified Eagle's medium (containing 10% BFS), various cells ($1\times10^5$ cells/dish) were incubated at 37° C. under 5% $CO_2$ atmosphere for 5~8 days. The cells were skeletal muscle cells differentiated from skeletal muscle myoblasts. The differentiated cells previously treated in serum-free Dulbecco's modified Eagle's medium for 4 hr were incubated with and without amylin (100 pM) before further incubation for 24 hr. Cultures treated with insulin (100 nM) thereafter were incubated for a fixed interval (10 or 60 min).

After the cultures were rinsed with ice-cold phosphate buffer, cells were lysed with phosphate buffer containing 0.5% octa (ethylene glycol) ether ($C_{12}E_8$). The pp140 was recovered by sepharobeads bound with phosphothyroid antibody (Transformation Corp.) prior to elution and detection with phenyl phosphate and western blotting method, respectively. The band content of pp140 was determined by a densitometer using purified pp140 as the standard. The results are illustrated in Table 1.

TABLE 1

Effects of p140 tyrosine phosphorylation on various tissues

|  | rat | | human | |
| --- | --- | --- | --- | --- |
|  | L6 | FaO | A 678 | HepG2 |
| control | 300 | 100 | 300 | 250 |
| insulin 10 min | 2400 | 2000 | 2500 | 2100 |
| insulin 60 min | 1000 | 1400 | 1900 | 1200 |
| insulin added amylin 10 min | 180 | 300 | 350 | 300 |
| insulin added amylin 60 min | 200 | 100 | 1000 | 300 |

In the Table 1, cultures were treated with amylin (100 pM) 24 hr before insulin (100 nM) was added.

Observation

Incidence of pp140, observed when rat L6 cells were incubated with insulin within 10 min, was antagonized by amylin treatment. Moreover, this phenomenon was similarly confirmed in rat hepatocytes, FaO cells. Furthermore, this phenomenon is not merely confined to rats. In human muscle cells (A673 cells) and hepatocytes (HepG2 cells), the phenomenon has been similarly confirmed. It is postulated that amylin suppresses a certain stage or processes before p140 phosphorylation is triggered by the phosphorylation signal of insulin.

EXAMPLE 3

Effects of various test compounds on p140 phosphorylation

Rat L6 cells ($1\times10^5$ cells/dish) were incubated in the Dulbecco's modified Eagle's medium (containing 10% BFS) at 37° C. under 5% $CO_2$ atmosphere for 8 days. The cells used were skeletal muscle myoblast-differentiated muscle cells. After treating the differentiated skeletal muscle cells in serum-free Dulbecco's modified Eagle's media for 4 hr, various test compounds (10 mM; except insulin, 1 mM) were added before the cultures were further incubated for a fixed interval.

After the cultures were rinsed with ice-cold phosphate buffer, cells were lysed with phosphate buffer containing 0.5% octa (ethylene glycol) ether ($C_2E_8$). The pp140 was recovered by cephalobeads bound with phosphotyrosine antibody (Transformation Corp.) prior to elution and detection with phenyl phosphate and western blotting method, respectively. The band content of pp140 was determined by a densitometer using purified pp140 as the standard. The results are illustrated in Table 2.

TABLE 2

Effects on p14O tyrosine phosphorylation of various test compounds

| | Amount of tyrosine phosphorylated p140 (copy/cell) (min) | | | |
| --- | --- | --- | --- | --- |
| Compound | 0 | 3 | 10 | 60 |
| Vitamin $K_3$ | 350 | 3650 | 1800 | 750 |
| Vitamin $K_5$ | 400 | 3850 | 2850 | 1600 |
| 5-phenylrhodanine | 350 | 1600 | 1250 | 650 |
| 5-benzylidenerhodanine | 400 | 2650 | 1900 | 1350 |
| 5-(4-isoamyloxybenzylidene) rhodanine | 400 | 3200 | 2250 | 1600 |
| Insulin (positive control) | 350 | 1850 | 2600 | 1650 |

EXAMPLE 4

Enhanced activity of glucose uptake

Rat L6 cells ($1\times10^5$ cells/dish) were incubated in Dulbecco's modified Eagle's medium (containing 10% BFS) at 37° C. under 5% $CO_2$ atmosphere for 8 days. The cells used were skeletal muscle myoblast-differentiated skeletal muscle cells. After treating the differentiated skeletal muscle cells in serum-free Dulbecco's modified Eagle's medium for 2 hr, various test compounds (10 mM; except insulin, 1 mM) were added before the cultures were further incubated for a fixed interval of 2 hr. Cultures thereafter treated with Crebs-Ringer phosphate buffer (pH: 7.4) for 20 min were further incubated with 5 mM $^3H$-2-deoxyglucose (0.05 mCi/ml). At the initial 3 min after incubation, the uptake radioactivity content in cells was determined with a liquid syntillation counter. The results are illustrated in Table 3.

TABLE 3

Enhanced activity of glucose uptake

| Compound | Activity on glucose uptake (pmol/mg protein/min) |
| --- | --- |
| Control | 22.6 |
| Vitamin $K_3$ | 60.9 |
| Vitamin $K_5$ | 67.5 |
| 5-phenylrhodanine | 76.8 |
| 5-benzylidenerhodanine | 84.2 |
| 5-(4-isoamyloxybenzylidene) rhodanine | 98.4 |

TABLE 3-continued

Enhanced activity of glucose uptake

| Compound | Activity on glucose uptake (pmol/mg protein/min) |
|---|---|
| Insulin (positive control) | 106.8 |

Observation

All compounds that promoted p140 phosphorylation were confirmed to activate glucose uptake activities (Table 2 and 3).

EXAMPLE 5

Figure 2:
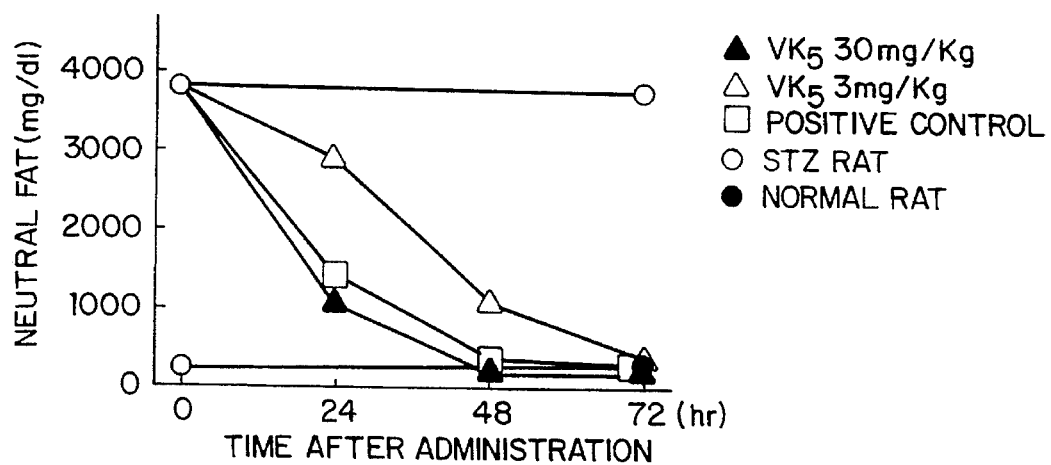
FIG. 2 shows an effects of vitamin $K_5$ ($VK_5$) on neutral fat contents in blood of streptozotocin (STZ)-induced diabetic rats
Figure 3:
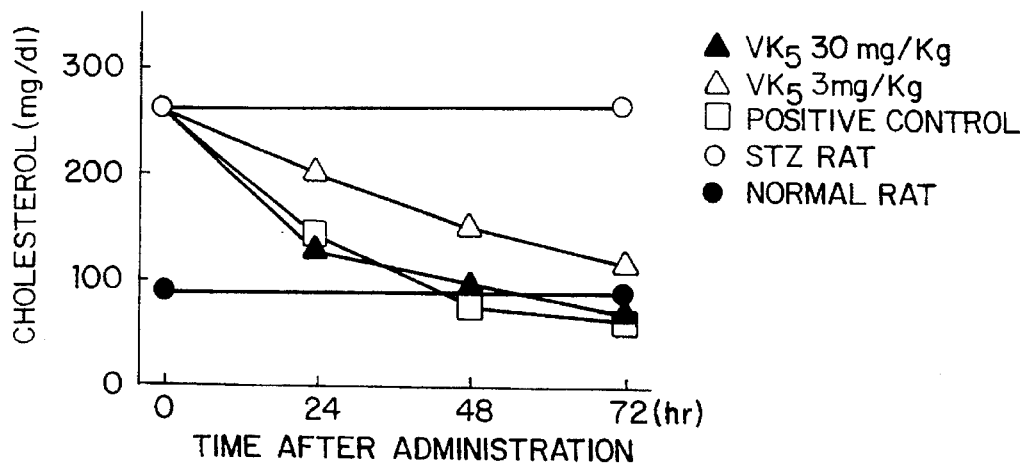
FIG. 3 shows an effects of vitamin $K_5$ ($VK_5$) on blood cholesterol contents in streptozotocin (STZ)-induced diabetic rats

Effects of vitamin $K_5$ on diabetes The diabetes model using streptozotocin (STZ) was established in male Wistar rats (STZ rats). After administering various intraperitoneal (i.p.) daily doses of vitamin $K_5$ for 3 consecutive days in STZ rats (one administration per day), the glucose, neutral fat and cholesterol contents in blood were determined. Accordingly, STZ and normal rats were administered with the vehicle (physiological saline) at an identical daily rate and duration prior to determination of similar hematic indices mentioned above. In addition, rats administered subcutaneously (s.c.) with insulin (8 U/kg) daily (one administration per day) for 3 consecutive days were used as positive controls. The results are shown in FIG. 1 to 3.

Observations

Administration with vitamin $K_5$ for 3 consecutive days elicited recovery of changes found in all hematic indices in rats; namely, the glucose, neutral fat and cholesterol contents.

EXAMPLE 6

Analysis of Partial amino acid sequence of pp140 pp140 purified in Example 1 was isolated by electrophoresis, followed by transcription in PVDF membrane, treatmented with trypsin and further isolated with liquid chromatography. The thus isolated pp140 fragment was then sequenced by using the 470A-model automated gas-phase protein sequences/120A-model PTH analyzer (ABI or Applied Biosystem Inc. Corp., U.S.A.) and the extensively employed Edman degradation method prior to determination of its partial amino acid sequence.

EXAMPLE 7

Partial amino acid sequencing of pp140 by the polymerase chain reaction (PCR) method By using extensively applied methods, various primers were derived from the thus isolated partial amino acid fragments, and their respective combinations were conducted before the PCR method was employed. The results revealed a specifically amplified fragment with an approximate length of 400 bp.

EXAMPLE 8

Isolation and purification of mRNA During the log growth phase, mRNA was isolated from $3 \times 10^7$ muscle myoblast L6 cells (ATCC strain No., CRL-1458) according to the method of Okayama et al (*Methods in Enzymology*, 154, 3 (1987)).

Briefly, after cells were lysed with 5.5 M GTC solution (5.5 M guanidine thiocyanate, 25 mM sodium citrate and 0.5% sodium lauryl sarcosine, the lysate was layered on cesium trifluoroacetate solution (density:1.51) cells lysate and centrifuged at 120,000× g for 20 hr before all the RNA in the pellet was recovered. The RNA sample was passaged through an oligo-dT-cellulose column twice prior to recovery by purification of 106 μg poly(A)$^{30}$ RNA.

EXAMPLE 9

Tissue distribution of p140 mRNA

From various tissues, poly(A)$^{30}$ RNA was purified according to procedures similar to those of Example 8. The respective tissue-derived poly(A)$^{30}$ RNA samples (each sample: 2 μg) were subjected to agarose-gel electrophoresis and subsequently transferred through a filter. The 2-kb open reading frame was labeled and used as the internal control before allowed to undergo normal hybridization. Autoradiography was conducted on the specifically bound probe and evaluated by densitometric analyses with an imaging analyzer. When the incidence of β-actin mRNA was taken 100 in the various tissues, relative contents of p140 in tissues are indicated in Table 4.

TABLE 4

Tissue distribution of p140 mRNA

| | rat | human |
|---|---|---|
| heart | 100 | 100 |
| brain | 240 | 60 |
| spleen | 70 | — |
| lungs | 210 | 100 |
| liver | 130 | 100 |
| muscles | 40 | 130 |
| kidneys | 130 | 40 |
| testes, | 320 | — |
| placenta | — | 220 |
| pancreas | — | 330 |

(—): represents experiments that were not done

Observation

Examination of all the various tissues studied reveals incidences of mRNA, whose effects are though to radiate over an extensive range of tissues. High incidence of mRNA is found especially in the human pancreas.

EXAMPLE 10

Establishing the cDNA library

A cDNA library was established according to the modified Gubler and Hoffman method (*Gene* 25, 263, (1983)).

From poly(A)$^{30}$ RNA (5 μg) derived in Example 2, a first strand was constructed with the reverse transcription enzyme, followed by transformation of a second strand with EcoRI adaptor ligation before excess adaptors and primers were eliminated by gel filtration column chromatography (Sephacryl S-500HR column; Pharmacia Corp.). The remaining 1,620 ng of cDNA fraction was subsequently recovered.

The above construction procedures for cDNA library were accomplished with a λgt 10 cloning system kit (Amersham Corp.).

Next, the λgt 10 phage (Amersham Corp.) and λZAPII phage (Stra Tagene Corp.) were ligated at the EcoRI-treated arms of 1.8-kb mean length. A phage cDNA library of an independent count of $3 \times 10^5$ was established.

EXAMPLE 11

Cloning and sequencing

Based on the phage DNA library established in Example 10, clones were duplicated to approximately $1 \times 10^5$ plagues/plate. The approximately 400-bp fragments harvested in Example 7 were designated as probes before screening was conducted. Of the positive controls, subcloning of long strands of the inserts in EcoRI side of plasmid vector pGEM-3Zf(+) (3199 bp; Promega Corp.) was established. T7 or SP6 was sequenced as the primer.

DNA sequencing based on the dideoxy terminator method was performed according to the cyclo-sequencing method using fluorescent di-terminator (ABI, USA). Furthermore, sequence reading was realized with a DNA sequencer (Model 373A; ABI, USA).

As such, nucleotide sequences of mean 300 bases were established from 5' or 3' side of the respective clone.

EXAMPLE 12

Partial sequence analysis

When the nucleotide sequence from Example 11 was subjected to a homology search with all the nucleotide sequences stored in previously registered data base (GenBank and EMBL) with the FASTA program of Lipman and Pearson, the sequenced clones would identify clones containing novel sequences. Nucleotide sequences of the identified clone were convened to amino acid sequences based on 3 possibly constructed frames.

Additionally, novel amino acid sequences in the amino acid sequences were also revealed.

However, the cDNA clone that has cloned does not necessarily cover the whole mRNA length. In such a case, the clone is most unlikely to contain the N terminal of amino acid sequence.

As such, the Northern analysis was used to determine if the whole length of the established clone was complemented. In other words, the poly(A)$^{30}$ RNA, isolated from Example 8 → Example 9 procedures by electrophoresis, was blotted on a nylon membrane. When the subcloned cDNA insert was hybridized as a probe, a single band at approximately 4400-bp position was observed. Since sizes of the clones were approximated to 2200 bp, PCR was performed at the 5' and 3' sides to read the whole cDNA length with the 3'-RACE (BRL Corp.) system and 5'-RACE (CLONTECH Corp.) system kits.

EXAMPLE 13

Determining the sequence and open reading frame of whole cDNA length

Random sequencing of the whole length of cDNA sequence was appropriated according to the method of Sambrook et al. (*Molecular Cloning*: ed. Sambrook J, Fritsch EF, Maniatis T; 1989, Cold Spring Harbor Laboratory Press).

Briefly, plasmid was recovered from the clone and the isolated cDNA insert was then purified before ligation and fragmentation. The termini of DNA fragments were further filled in by T4 polymerase and fragments of approximated 400obp length were recovered by agarose electrophoresis. DNA fragments thus established were subjected to cloning in the SmaI side of plasmid vector and pGEM-3Zf(+) (3199 bp; Promega Corp.) before transformation in *E. Coli*. Eighty colonies were picked up at random and plasmid DNAs were refined prior to DNA sequencing of these 20 plasmids (possessing cDNA fragments as inserts). DNA sequencing and sequence reading were performed according to the method dscribed in Example 11. Sequence data of cDNA fragments were constructed to the linkage sequences with the DNA sequence program of DNASIS. The basic sequence portrayed in Seq. ID No 3 was hence constructed. From sequence data of the whole cDNA length, the open reading frame (ORF) was determined. The amino acid sequence was further translated and the sequence thus established is illustrated in Seq. ID No 1. One of the frames possesses the 2993-bp ORF, that was approximated to 3,000 bp of the whole ORF length of the Eck family. Therefore, the said polypeptide in the present invention is postulated to possess a whole length of 2,993 bp.

Figure 4:
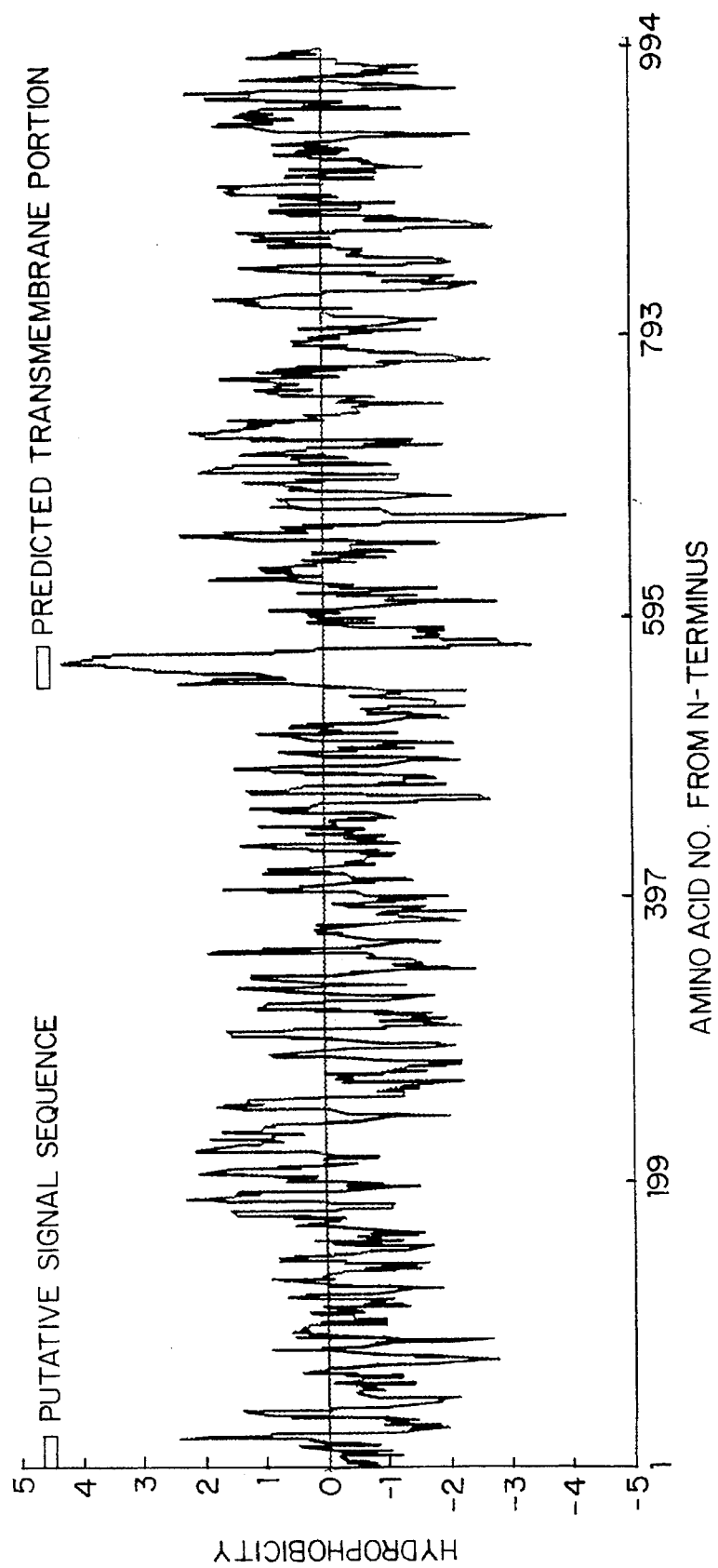
FIG. 4 shows a hydrophobicity profile for the polypeptide of protein p140 in the present invention

Based on its hydrophobicity, protein p140 was further postulated to be a typical Type I membrane protein (FIG. 4 demarcates the zone with either high (+) or low (−) hydrophobicity).

All in all, the said p140 polypeptide is a typical membrane protein with 993 amino acids and the length of its ORF is 2982 bp. Furthermore, the estimated molecular weight of the said p140 polypeptide is 109,860 Da, and is 140 kD when evaluated with its polysaccharide chain.

EXAMPLE 14

Construction of plasmid vector for using the preparation of expression vector

As an expression vector, pUC-SRαML-1 (This vector is disclosed itself and preparation thereof in European Patent publication No. 559428) derivative was used. This derivative was constructed to insert two kinds of fragments as shown below:

| fragment T7 | 5' GTAATACGACTCACTATAGGGGAGAGCT 3' | (SEQ ID No. 8) |
|---|---|---|
| | 3' ACGTCATTATGCTGAGTGATATCCCCTC 5' | (SEQ ID No. 9) |
| | between PstI and SacI and | |
| fragment SP6 | 5' CTAGTCTATAGTGTCACCTAAATCGTGGGTAC 3' | (SEQ ID No. 10) |
| | 3' AGATATCACAGTGGATTTAGCAC 5' | (SEQ ID No. 11) |
| | between SpeI and KpnI site in the multi-cloning site, respectively. | |

Figure 5:
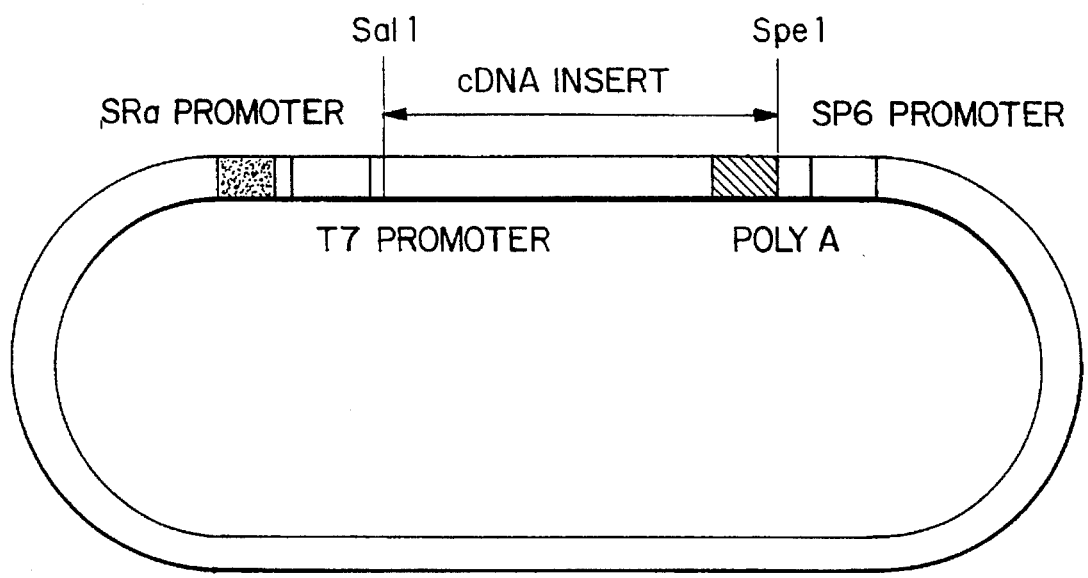
FIG. 5 shows the pUCSRαML2 vector.

The pUC-SRαML1 vector was digested with PstI and SacI and the resulting digest was subjected to agarose gel electrophoresis to prepare and recover an about 4.1 kbp fragment and thereafter removing the 5'-end phosphoric acid group by BAP (bacterial alkaline phosphatase) treatment. The phosphorylated DNA fragment T7 was ligated with the thus prepared about 4.1 kbp fragment from pUC-SRαML1 to make them into a circular form. The resulting vector was, moreover, digested with SpeI and KpnI and the resulting digest was subjected to agarose gel electrophoresis to prepare and recover an about 4.1 kbp fragment and thereafter removing the 5'-end phosphoric acid group by BAP (bacterial alkaline phosphatase) treatment. The phosphorylated DNA fragment SP6 was ligated with the thus prepared about 4.1 kbp fragment to make them into a circular form. The plasmid vector constructed in this manner was named pUC-SRαML2 (See FIG. 5).

EXAMPLE 15

Construction of expression vector The primers X, Y and YH, that aneal to rat p140 cDNA were synthesized. Sequences of primers X, Y and YH are as follows:

Primer X

5'- A ATA TAG TCG ACC ACC ATG GAG AAC CCC TAC GTT GGG CGA GCG A -3'  (SEQ ID No. 12)

Primer Y

5'- CGG CGG ACT AGT TCA GAC CTG CAC GGG CAG TGT CTG G -3'  (SEQ ID No. 13)

Primer YH

5'- GCC GCC ACT AGT TCA GTG GTG GTG GTG GTG GTG GAC CTG CAC GGG CAG TGT CTG G -3'  (SEQ ID No. 14)

The plasmid containing cDNA of p140 was subjected to PCR using the thus synthesized oligonucleotides X and Y as templates. The thus obtained PCR fragment contains a sequence placed 5'-adjacent to the initiation codon, that corresponds to the Cozac sequence known among those skilled in the art, and cDNA which encodes a protein molecule consisting of the p140 protein. The PCR fragment was digested with SalI-SpeI and the resulting digest was separated and purified and then inserted into the SalI-SpeI site of the pUC-SRαML2 prepared in Example 14 to obtain an expression vector pUC-SRαML2-p140-A.

Moreover, the plasmid containing cDNA of p140 was subjected to PCR using the synthesized oligonucleotides X and YH as templates. The thus obtained PCR fragment contains a sequence placed 5'-adjacent to the initiation codon, that corresponds to the Cozac sequence known among those skilled in the art, and cDNA which encodes a protein molecule consisting of the p140 protein and six additional histidine (His) residues attached to its C-terminal end. The PCR fragment was digested with SalI-SpeI and the resulting digest was separated and purified and then inserted into the SalI-SpeI site of the pUC-SRαML2 prepared in Example 14 to obtain an expression vector pUC-SRαML2-p140-B.

Moreover, primer Z and ZH were synthesized. Sequences of primer Z and ZH are as follows: (These were adjoined to amino-terminal end of transmembrane region in cDNA.)

codon, that corresponds to the Cozac sequence known among those skilled in the art, and cDNA which encodes a polypeptide consisting of the p140 protein extracellular part and six additional histidine (His) residues attached to its C-terminal end. The PCR fragment was digested with SalI-SpeI and the resulting digest was separated and purified and then inserted into the SalI-SpeI site of the pUC-SRαML2 prepared in Example 14 to obtain an expression vector pUC-SRαML2-p140-D.

Each of the thus constructed pUC-SRαML2-p140-A, pUC-SRαML2-p140-B, pUC-SRαML2-p140-C and pUC-SRαML2-p140-D plasmids were transfected into an *E. coli* strain DH5, recovered from a 100 ml culture of the resulting transformant and then purified twice with CsCl density gradient centrifugation.

EXAMPLE 16

Expression in COS cells

Each of the plasmid DNA preparations pUC-SRαML2, pUCSRαML2-p140-A, pUC-SRαML2-p140-B, pUC-SRαML2-p140-C and pUC-SRαML2-p140-D were introduced into COS-7 cells (*Cell*, 23, 175 (1981)) by means of the diethylaminoethyl (DEAE) dextran method (*J. Immunology*, 136, 4291 (1986)).

That is, about $1.8 \times 10^6$ COS-7 cells were inoculated into a 225 cm$^2$ capacity flask (manufactured by Corning) together with 50 ml of a liquid culture medium (Dulbecco's

Primer Z

5'- CGG CGG ACT AGT TCA TGA GCC TCT TTC ACT CGT GGT CTC AAA CT -3'  (SEQ ID No. 15)

Primer ZH

5'- GCC GCC ACT AGT TCA GTG GTG GTG GTG GTG GTG TGA GCC TCT TTC ACT CGT GGT CTC AM CT -3'  (SEQ ID No. 16)

The plasmid containing cDNA of p140 was subjected to PCR using the thus synthesized oligonucleotides X and Z as templates. The thus obtained PCR fragment contains a sequence placed 5'-adjacent to the initiation codon, that corresponds to the Cozac sequence known among those skilled in the art, and cDNA which encodes a polypeptide consisting of the p140 protein extracellular part. The PCR fragment was digested with SalI and NotI and the resulting digest was separated and purified and then inserted into the SalI-SpeI site of the pUC-SRαML2 prepared in Example 14 to obtain an expression vector pUC-SRαML2-p140-C.

Moreover, the plasmid containing cDNA of p140 was subjected to PCR using the synthesized oligonucleotides X and ZH as templates. The thus obtained PCR fragment contains a sequence placed 5'-adjacent to the initiation modified MEM medium supplemented with 10% decomplemented fetal bovine serum). After overnight incubation in a carbon dioxide incubator (37° C., 5% CO$_2$) and subsequent removal of the culture supernatant, 12 ml of a DNA cocktail (Dulbecco's modified MEM medium supplemented with 15 μg of each plasmid DNA, 50 mM Tris-HCl buffer (pH 7.4) and 400 μg/ml of DEAE-dextran) was added to each flask and culture was carried out for 3 hours at 37° C. in an atmosphere of 5% CO$_2$. Thereafter, the DNA cocktail was replaced by 15 ml of a chloroquine solution (Dulbecco's modified MEM medium supplemented with 150 μM chloroquine and 7% decomplemented fetal bovine serum), followed by an additional 3 hours of culture.

After removing the chloroquine solution, the aforementioned liquid culture medium (50 ml) was added to each of the resulting flasks which were then incubated at 37° C. in an atmosphere of 5% $CO_2$ for 72 hours to allow growth of the cells in each flask to reach almost monolayer form. After removing the culture supernatant, the cells in each flask were washed with a serum-free liquid culture medium (trade name, SFM-101; available from Nissui Pharmaceutical Co., Ltd.) and then supplied with 75 ml of the same serum-free liquid culture medium, and the culturing was continued for another 72 hours. Thereafter, the resulting culture supernatants were recovered and cells were lysed as represented in Example 1. These supernatants and cell lysates were filtered through a membrane filter (trade name, STERIVEX-GS; available from Millipore Corp.) to remove cell debris. The thus obtained culture supernatant samples were stored at 4° C. for future use. The cell lysates of COS cells which have been transformed with plasmid containing the pUC-SRαML2-p140-A and pUC-SRαML2-p140-B inserts are expected to contain expressed mature protein moieties of polypeptides which correspond to p140 protein. And culture supernatants of COS cells which have been transformed with plasmid containing the pUC-SRαML2-p140-C and pUC-SRαML2-p140-D inserts are expected to contain secreted polypeptides which correspond to p140 protein extracellular part.

EXAMPLE 17

Confirmation of expression

A 2 ml portion of each of the culture supernatants of transformed COS cells obtained in Example 16 was concentrated to a volume of 100 ml using a centrifugal concentration filter (trade name, Centricon-10; available from Millipore Corp.). A 1 μl portion of each of the thus concentrated samples was mixed with the same volume of a loading buffer (0.125M Tris-HCl buffer (pH 6.8), 4% sodium dodecyl sulfate and 30% glycerol) for SDS-PAGE (sodium dodecyl sulfate polyacrylamide gel electrophoresis) use, and the mixture was treated at 90° C. for 3 minutes and then subjected to SDS-PAGE.

In the case of the pUC-SRαML2-p140-B and pUC-SRαML2-p140-D proteins having His hexamer introduced to the C-terminus of the proteins, not only their corresponding cell lysates and COS cell culture supernatants but also their purified products were subjected to the SDS-PAGE analysis.

Purification of the protein was carried out by means of a metal chelate affinity chromatography (*Biotechnology*, 9, 273, (1991)), making use of the function of His to form complex compounds with various transition metal ions. That is, a culture supernatant (350 ml) or cell lysates (100 ml) obtained from COS cells was mixed with a sodium chloride aqueous solution in such an amount that the final concentration of the salt became 1M, and the resulting mixture was applied to a column packed with 4 ml of a zinc-linked chelating Sepharose (trade name, Chelating Sepharose Fast-Flow; available from Pharmacia) to adsorb the protein to the resin. The column was washed with 50 mM phosphate buffer (pH 7.0) containing 1M sodium chloride aqueous solution (40 ml), and the protein retained in the column was eluted with 50 mM phosphate buffer (pH 7.0) containing 1M sodium chloride aqueous solution and 0.4M imidazole. Thereafter, the resulting elute was concentrated to a volume of 100 μl, and a portion of the concentrated sample was subjected to SDS-PAGE analysis.

The SDS-PAGE analysis was carried out using a SDS 10/20 gradient gel and a product which corresponds to a molecular weight of p140 was detected in samples prepared from COS cells transfected pUC-SRαML2-p140-A and p140-B. Furthermore, a polypeptide which corresponds to a molecular weight of the extracellular portion of p140 was detected in untreated and purified supernatants, not cell lysates, prepared from COS cells transfected pUC-SRαML2-p140-C and p140-D.

Formulation Example 1

The following components were admixed in a conventional method and punched out to obtain 100 tablets each containing 5 mg of active ingredient.

| | |
|---|---|
| Vitamin $K_5$ | 500.0mg |
| Carboxymethylcellulose calcium | 200.0mg |
| Magnesium stearate | 100.0mg |
| Microcrystalline cellulose | 9.2mg |

While the invention has been described in detail and with reference to specific embodiments thereof, it will be apparent to one skilled in the art that various changes and modifications can be made therein without departing from the spirit and scope thereof.

We claim:

1. A polypeptide of protein p140 having the amino acid sequence shown in SEQ ID No. 1 in substantially purified form.

2. A pharmaceutical composition containing a polypeptide according to claim 1 in association with a pharmaceutically acceptable diluent and/or carrier.

* * * * *